US011295833B2

(12) United States Patent
Baba

(10) Patent No.: US 11,295,833 B2
(45) Date of Patent: Apr. 5, 2022

(54) ANALYSIS METHOD FOR GLYCOPROTEINS

(71) Applicant: DH TECHNOLOGIES DEVELOPMENT PTE. LTD., Singapore (SG)

(72) Inventor: Takashi Baba, Richmond Hill (CA)

(73) Assignee: DH Technologies Development Pte. Ltd., Singapore (SG)

(*) Notice: Subject to any disclaimer, the term of this patent is extended or adjusted under 35 U.S.C. 154(b) by 0 days.

(21) Appl. No.: 17/042,108

(22) PCT Filed: Mar. 19, 2019

(86) PCT No.: PCT/IB2019/052229
§ 371 (c)(1),
(2) Date: Sep. 26, 2020

(87) PCT Pub. No.: WO2019/186322
PCT Pub. Date: Oct. 3, 2019

(65) Prior Publication Data
US 2021/0104299 A1    Apr. 8, 2021

Related U.S. Application Data

(60) Provisional application No. 62/650,279, filed on Mar. 29, 2018.

(51) Int. Cl.
*G16B 40/10*    (2019.01)
*G16C 20/20*    (2019.01)
(Continued)

(52) U.S. Cl.
CPC ........ *G16B 40/10* (2019.02); *G01N 33/6848* (2013.01); *G16C 20/20* (2019.02);
(Continued)

(58) Field of Classification Search
CPC ....... G16B 40/10; G16C 20/20; H01J 49/005; H01J 49/0054; H01J 49/0036; G01N 33/6848
See application file for complete search history.

(56) References Cited

U.S. PATENT DOCUMENTS

2010/0314537 A1* 12/2010 McLuckey .......... H01J 49/0072
250/282
2014/0099725 A1* 4/2014 Williams ............... G01N 27/62
436/87

OTHER PUBLICATIONS

International Search Report and Written Opinion for PCT/IB2019/052229, dated Aug. 2, 2019.
(Continued)

*Primary Examiner* — Wyatt A Stoffa
(74) *Attorney, Agent, or Firm* — Kasha Law LLC; John R. Kasha; Kelly L. Kasha

(57) ABSTRACT

A mass isolation device selects a precursor ion of a sample that has been digested using a protease. A first fragmentation device fragments the precursor ion using collision-induced dissociation (CID), and the resulting product ions are analyzed using a mass analyzer producing a CID spectrum. A list of theoretical candidate glycopeptide sequences is determined from CID spectrum. The mass isolation device again selects the precursor ion of the sample. A second fragmentation device fragments the precursor ion using electron-based dissociation (ExD), and the resulting product ions are analyzed using the mass analyzer producing a CID spectrum. For each sequence of the list, the sequence is computationally fragmented, producing theoretical fragments, mass-to-charge ratio (m/z) values are calculated for the theoretical fragments, and the sequence is scored using c and z fragment matching rules. The highest scoring sequence is identified as a peptide sequence of a glycopeptide of the sample.

21 Claims, 16 Drawing Sheets

(51) Int. Cl.
*G01N 33/68* (2006.01)
*H01J 49/00* (2006.01)

(52) U.S. Cl.
CPC ........ *H01J 49/005* (2013.01); *H01J 49/0036* (2013.01); *H01J 49/0054* (2013.01); *H01J 49/0068* (2013.01)

(56) References Cited

OTHER PUBLICATIONS

Lin, Zhenxin et al., "An N-glycosylation analysis of human alpha-2-macroglobulin using an integrated approach", Journal of Proteomics & Bioinformatics, 2012, vol. 5, Issue 5, pp. 127-134.

Thaysen-Andersen, Morten et al., "Advances in LC-MS/MS-based glycoproteomics: getting closer to system-wide site-specific mapping of the N-and O-glycoproteome", Biochimica et Biophysica Acta (BBA)—Proteins and Proteomics, 2014, vol. 1844, pp. 1437-1452.

Kolli, Venkata et al., "Ion mobility-resolved collision-induced dissociation and electron transfer dissociation of N-glycopeptides: gathering orthogonal connectivity information from a single mass-selected precursor ion population", Analyst, 2017, vol. 142, pp. 4691-4702.

\* cited by examiner

ANALYSIS METHOD FOR GLYCOPROTEINS

CROSS REFERENCE TO RELATED APPLICATIONS

This application claims the benefit of U.S. Provisional Patent Application Ser. No. 62/650,279, filed Mar. 29, 2018, the content of which is incorporated by reference herein in its entirety.

INTRODUCTION

The teachings herein relate to operating a tandem mass spectrometer to identify glycoproteins in a sample. More specifically, systems and methods are provided for operating a tandem mass spectrometer to perform both electron-based dissociation (ExD) and collision-induced dissociation (CID) and combining the data of these two techniques to identify one or more glycoproteins in a sample.

The systems and methods herein can be performed in conjunction with a processor, controller, or computer system, such as the computer system of FIG. 1.

Glycans, Glycoproteins, and Glycopeptides

In general, a glycan is a polysaccharide, which is a molecule made up of a number of simple sugars or monosaccharides. Sugars or monosaccharides are the basic building blocks of carbohydrates. In a biological process known as glycosylation, glycans, or more specifically polysaccharide residues, are added to proteins in vivo. Such a process is commonly referred to as a post-translational modification (PTM). In other words, a protein is modified to include a glycan after it is translated or created within a cell. The protein resulting from PTM is referred to as a glycoprotein. Subunits or pieces of a glycoprotein that result from processes such as digestion are referred to as glycopeptides.

Glycosylation is used by cells in many ways including in cellular communication. It is known that in many disease processes, such as cancer, abnormal glycosylation occurs. As a result, the identification of abnormal glycosylation of certain proteins can be used to diagnose these disease processes.

Unfortunately, however, the identification of any glycoprotein produced in the body is confounded by the sheer number of possible combinations of different glycans. In the case of humans, at least 300 different common glycans have been reported. However, the number of possible different glycan's is actually many times larger due to the fact that further attachment of sugars to the common glycans multiplies the total number many times over.

Glycoproteomic Mass Spectrometry

The study or identification of glycoproteins can be referred to as glycoproteomics. Tandem mass spectrometry is a general tool for use in glycoproteomics given its proven track record in proteomics. Mass spectrometry (MS) or mass spectrometry/mass spectrometry (MS/MS) (herein also referred to as tandem mass spectrometry) can be used to identify glycoproteins in a sample.

In a typical MS or tandem mass spectrometry glycoproteomic experiment, a sample that includes one or more glycoproteins is first digested by enzymes such as trypsin. As a result, some of the digested peptides of the glycoproteins proteins have glycans attached. These peptides that have attached glycans are referred to as glycosylated peptides or glycopeptides. Each glycopeptide includes a sequence of amino acids, which is the peptide part, at least one glycan structure, and a modification site on the peptide where the at least one glycan structure is attached. MS or tandem mass spectrometry is then used to identify the peptide sequence, glycan structure, and the modification site.

Peptide Identification Through Fragmentation

Tandem mass spectrometry implies fragmentation or dissociation of ions. In tandem mass spectrometry, the first mass spectrometry step is the selection of an ion called the precursor ion and the second mass spectrometry step is the fragmentation or dissociation of that precursor ion into one or more product ions.

Tandem mass spectrometer systems are useful in identifying peptides through fragmentation. Peptides are molecules that are sequences of amino acids having an amino group located on one end of the molecule and a carboxylic acid located at the other end. When subjected to fragmentation processes within a tandem mass spectrometer system, the peptide chains can be cleaved at their peptide bonds, forming individual fragments of the original peptide. Various types of fragmentation processes can occur, the most common being collision induced dissociation (CID) common in tandem mass spectrometers, in which molecules collide with a gas. Other types of dissociation processes are also known, such as electron capture dissociation (ECD) and electron transfer dissociation (ETD), among others.

The resulting fragment or product ions can be labeled with reference to either the amino or acidic end (termed the N-terminus and C-terminus, respectively) of the original peptide along with the number of amino acid units (i.e., residues) that the fragment includes.

Peptide fragments known as "b-ions" are fragments with the N-terminus. A subscript denotes the number of amino acid residues from the original peptide that are included in the fragment. Thus, a $b_4$ ion is a fragment ion of a peptide (precursor ion) that contains the four amino acid residues from the N terminus of the original peptide. Similarly, "y-ions" are fragments with the C-terminus and are counted similarity.

Fragments can also be defined as being a-ions and c-ions which are related to b-ions but designate cleavage at a slightly differently location. A-ions are b-ions minus the C=O, whereas C-ions are b-ions plus the N—H group. Similarly, z-ions are y-ions minus the N—H group, whereas x-ions are y-ions plus C=O.

The mass of a fragment or product ion can be determined in part by summing the residue masses of the respective amino acids that make up the fragment. Therefore, a mass spectrum of a peptide that has been subjected to dissociation contains information that may be used to determine the overall amino acid sequence of the peptide.

Glycosylation Types

There are two types of glycosylation that often appear. These are N-glycosylation and O-glycosylation. An N glycan is attached on an asparagine residue (N) with consensus sequences asparagine-X-serine or asparagine-X-threonine, where X can be any amino acid residue except proline. An O glycan is attached on a serine residue (S) or threonine residue (T). There is no additional consensus sequence for O-glycosylations, so single residue S and T consensus sequences are referred to as the consensus sequences for O-glycosylation in this application.

Dissociation Techniques

Electron-based dissociation (ExD) and collision induced dissociation (CID) are often used as dissociation techniques for tandem mass spectrometry glycopeptide analysis. ExD can include, but is not limited to, ECD (electron capture dissociation) or ETD (electron transfer dissociation). CID is the most conventional technique for dissociation in mass spectrometers. ExD and CID are complimentary techniques for glycopeptide analysis. ExD dissociates peptide backbones preferentially, so it is an ideal tool to analyze peptide sequences. CID, on the other hand, dissociates glycans preferentially, so it is a useful tool to analyze glycan structure Glycan analysis using CID is well known to one skilled in the art because CID based MS instruments are quite common and have been used for this type of analysis for a long time. Peptide back bone analysis has been demonstrated using ECD in Fourier transform ion cyclotron resonance (FT-ICR) mass spectrometers, ECD in ion traps, and ETD and other devices. However, ExD, in general, is not a well-explored area of mass spectrometry due to the following difficulties.

For example, FT-ICR mass spectrometers with an ECD option are not widely used in the industry because the instrument is too big, too expensive, and difficult to operate. Similarly, an ETD device may be able to cleave peptide back bone, but the dissociation efficiency is too low to perform high throughput LC-MS/MS analysis. In addition, for ECD in an ion trap, high dissociation efficiency has been demonstrated using hot ECD, where an electron kinetic energy of from a few eV to 10 eV was applied.

Recently, however, high throughput hot ECD analysis on glycopeptides with intact glycans was demonstrated using a Chimera ECD device developed by Sciex with an electron energy of 7 eV. This device is described in co-pending U.S. Published Patent Application No. 2016/0126076, which is herein incorporated by reference.

Glycan Database Matching Problem

Conventionally, a tandem mass spectrometry protein identification experiment has involved digesting at least one protein of a sample into peptides, fragmenting each of the peptides found, and producing a product ion spectrum for each of the peptides. The product ion spectra of the peptides found are then compared to a protein database to identify the protein.

Unfortunately, as described above, this method of identification cannot be applied to glycoproteins due to the large number of possible different glycoproteins. In other words, the difficulty comes from the fact that there are too many (almost an infinite number) different possible glycan structures. In conventional database searching programs, such as MASCOT, search field (or candidates of surveying peptide sequences) or calculation time is reduced using the precursor mass information of the analyzing spectrum. This method works well if assumed PTMs are simple, such as phosphorylation or methylation. The additional mass of such possible modifications is mathematically attached at possible modification sites before selecting the candidate peptide sequences from the entire list of candidate peptides given by the genome. Unfortunately, this method encounters difficulty when trying to handle glycosylations because there are just too many candidate modifications. As described above, in the case of humans, 300 common glycans are reported, but the actual number is almost infinitely larger due to the further attachment of sugars on the common glycans.

Separate CID or ExD Dissociation

One approach to this difficulty is to trim the glycans before mass analysis. Glycans are trimmed using enzymes. In the case of N-glycosylations, all glycans are often removed by enzymes (peptide-N glycosidase F, PNGase F) or (peptide-N glycosidase A, PNGase A). Using these enzymes, the modified asparagine is converted to an aspa-rate, so this change can be detected by CID based mass analysis. Modification sites can be determined. However, glycan information is lost.

In case of O glycans, if all glycans are removed by enzymes, no glycosylation trace remains on modified the modified S and T residues. This means both information of modification sites and the glycans is lost. As a result, CID is not used for O glycan analysis alone.

In contrast, ExD works on a peptide back bone and O glycans remain attached on the back bone after dissociation is applied. However, the only type of conventional database searching that can be applied is to assume that the glycans are very simple such as MUC core 1 (Gal-GalNAc), core 2 (GlcNAc-GalNAc-Gal), core 3 (GlcNAc-GalNAc) and core 4 (GlcNAc-GalNAc GlcNAc), where GalNAc is bound to peptides. Unfortunately, this method is not very useful, since it does not cover many types of O glycans.

Combined CID and ExD Dissociation

One approach to solving glycan database matching problem has been to perform two or more different dissociation techniques on the same sample and combine the results to determine the glycoproteins. For example, Mayampurath et al. have described in their paper entitled "Computational Framework for Identification of Intact Glycopeptides in Complex Samples," Anal. Chem. 2014, 86, 453-463 (hereinafter the "Mayampurath Paper") that glycoprotein identification has been improved by combining ETD/CID spectra of the same precursor ion. Mayampurath et al. also describes a method in which data or scores from CID, ETC, and higher-energy C-trap dissociation (HCD) are combined to identify glycopeptides. Mayampurath et al. calculate separate CID, ETC, and HCD scores from mapping a glycopeptide candidate to CID, ETC, and HCD spectra, respectively. Glycopeptide candidates are constructed by attaching each N glycan from a glycan list to peptides containing sequons obtained from an in silico tryptic digest. In other words, the technique is still limited by the number of glycans in its glycan list.

Although combining two or more tandem mass spectrometry complementary dissociation techniques appears to be a possible solution to glycoprotein or glycopeptide identification, no method to combine the data from two or more tandem mass spectrometry complementary dissociation techniques currently exists that completely addresses the glycan database matching problem.

Consequently, there is a need for systems and methods to control or operate a tandem mass spectrometer capable of performing two or more tandem mass spectrometry complementary dissociation techniques and combining their data to identify one or more glycoproteins in a sample.

Tandem Mass Spectrometry Background

In general, tandem mass spectrometry, or MS/MS, is a well-known technique for analyzing compounds. Tandem mass spectrometry involves ionization of one or more compounds from a sample, selection of one or more precursor ions of the one or more compounds, fragmentation of the one or more precursor ions into fragment or product ions, and mass analysis of the product ions.

Tandem mass spectrometry can provide both qualitative and quantitative information. The product ion spectrum can be used to identify a molecule of interest. The intensity of one or more product ions can be used to quantitate the amount of the compound present in a sample.

LC-MS and LC-MS/MS Background

The combination of mass spectrometry (MS) (or mass spectrometry/mass spectrometry (MS/MS)) and liquid chromatography (LC) is an important analytical tool for identification and quantification of compounds within a mixture. Generally, in liquid chromatography, a fluid sample under analysis is passed through a column filled with a solid adsorbent material (typically in the form of small solid particles, e.g., silica). Due to slightly different interactions of components of the mixture with the solid adsorbent material (typically referred to as the stationary phase), the different components can have different transit (elution) times through the packed column, resulting in separation of the various components. In LC-MS, the effluent exiting the LC column can be continuously subjected to mass spectrometric analysis to generate an extracted ion chromatogram (XIC) or LC peak, which can depict detected ion intensity (a measure of the number of detected ions, total ion intensity or of one or more particular analytes) as a function of elution or retention time.

In some cases, the LC eluate can be subjected to tandem mass spectrometry (or mass spectrometry/mass spectrometry MS/MS) for the identification of product ions corresponding to the peaks in the XIC. For example, the precursor ions can be selected based on their mass/charge ratio to be subjected to subsequent stages of mass analysis. The selected precursor ions can then be fragmented (e.g., via collision induced dissociation (CID), electron capture dissociation (ECD)), and the fragmented ions (product ions) can be analyzed via a subsequent stage of mass spectrometry.

Tandem Mass Spectrometry Acquisition Methods

A large number of different types of experimental acquisition methods or workflows can be performed using a tandem mass spectrometer. Three broad categories of these workflows are targeted acquisition, information dependent acquisition (IDA) or data-dependent acquisition (DDA), and data-independent acquisition (DIA).

In a targeted acquisition method, one or more transitions of a precursor ion to a product ion are predefined or known for a compound of interest. As a sample is being introduced into the tandem mass spectrometer, the one or more transitions are interrogated during each time period or cycle of a plurality of time periods or cycles. In other words, the mass spectrometer selects and fragments the precursor ion of each transition and performs a targeted mass analysis for the product ion of the transition. As a result, an intensity (a product ion intensity) is produced for each transition. Targeted acquisition methods include, but are not limited to, multiple reaction monitoring (MRM) and selected reaction monitoring (SRM).

In an IDA method, a user can specify criteria for performing an untargeted mass analysis of product ions, while a sample is being introduced into the tandem mass spectrometer. For example, in an IDA method, a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS can be repeatedly performed on the precursor ions of the subset of precursor ions as the sample is being introduced into the tandem mass spectrometer.

In proteomics and many other sample types, however, the complexity and dynamic range of compounds are very large. This poses challenges for traditional targeted and IDA methods, requiring very high-speed MS/MS acquisition to deeply interrogate the sample in order to both identify and quantify a broad range of analytes.

As a result, DIA methods, the third broad category of tandem mass spectrometry, were developed. These DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead, a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

SUMMARY

A system, method, and computer program product are disclosed for operating tandem mass spectrometer to identify a peptide sequence of a glycopeptide of a sample. The tandem mass spectrometer includes a mass isolation device, a first fragmentation device, a second fragmentation device, and a mass analyzer. All three embodiments include the following steps.

A mass isolation device of a tandem mass spectrometer (MS/MS) is instructed to select at least one precursor ion from a first ion beam using a processor. The first ion beam is produced by an ion source device adapted to receive and ionize a sample that has been digested using a protease. A first fragmentation device of the MS/MS that is adapted to fragment selected precursor ions using collision-induced dissociation (CID) is instructed to fragment the at least one precursor ion using the processor, producing a plurality of CID product ions. A mass analyzer of the MS/MS is instructed to mass analyze the plurality of CID product ions using the processor, producing a first CID spectrum. A list of one or more theoretical candidate glycopeptide sequences that can be glycosylated is determined from the first CID spectrum using the processor.

The mass isolation device is instructed to select again the at least one precursor ion from a second ion beam produced by the ion source device from the sample using the processor. A second fragmentation device of the MS/MS that is adapted to fragment selected precursor ions from the second ion beam using electron-based dissociation (ExD) is instructed to fragment the at least one precursor ion using the processor, producing a plurality of ExD product ions. The mass analyzer is instructed to mass analyze the plurality of ExD product ions using the processor, producing an ExD spectrum.

For each candidate sequence of the list, the sequence is computationally fragmented using c and z fragment rules (or ExD fragmentation rules), producing a plurality of theoretical fragments, mass-to-charge ratio (m/z) values are calculated for the plurality of theoretical fragments and the theoretical m/z value and ExD spectrum are compared. The likeliness between the ExD spectrum and a sequence candidate is scored using the processor. The sequence is scored by (a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site, (b) not incrementing the score, for each m/z value of a product ion peak of the ExD spectrum that matches to an m/z value of a z fragment of the plurality of theoretical fragments from the N terminal side of the sequence to a consensus sequence of a glycan modification site, (c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and (d) incrementing the score, for each m/z value of a product ion peak of the ExD spectrum that matches to an m/z value of a z fragment of the plurality of theoretical fragments from the C terminal side of the sequence to a consensus sequence of a glycan modification site.

A candidate sequence of the list with the highest score is identified as a peptide sequence of a glycopeptide of the sample using the processor.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
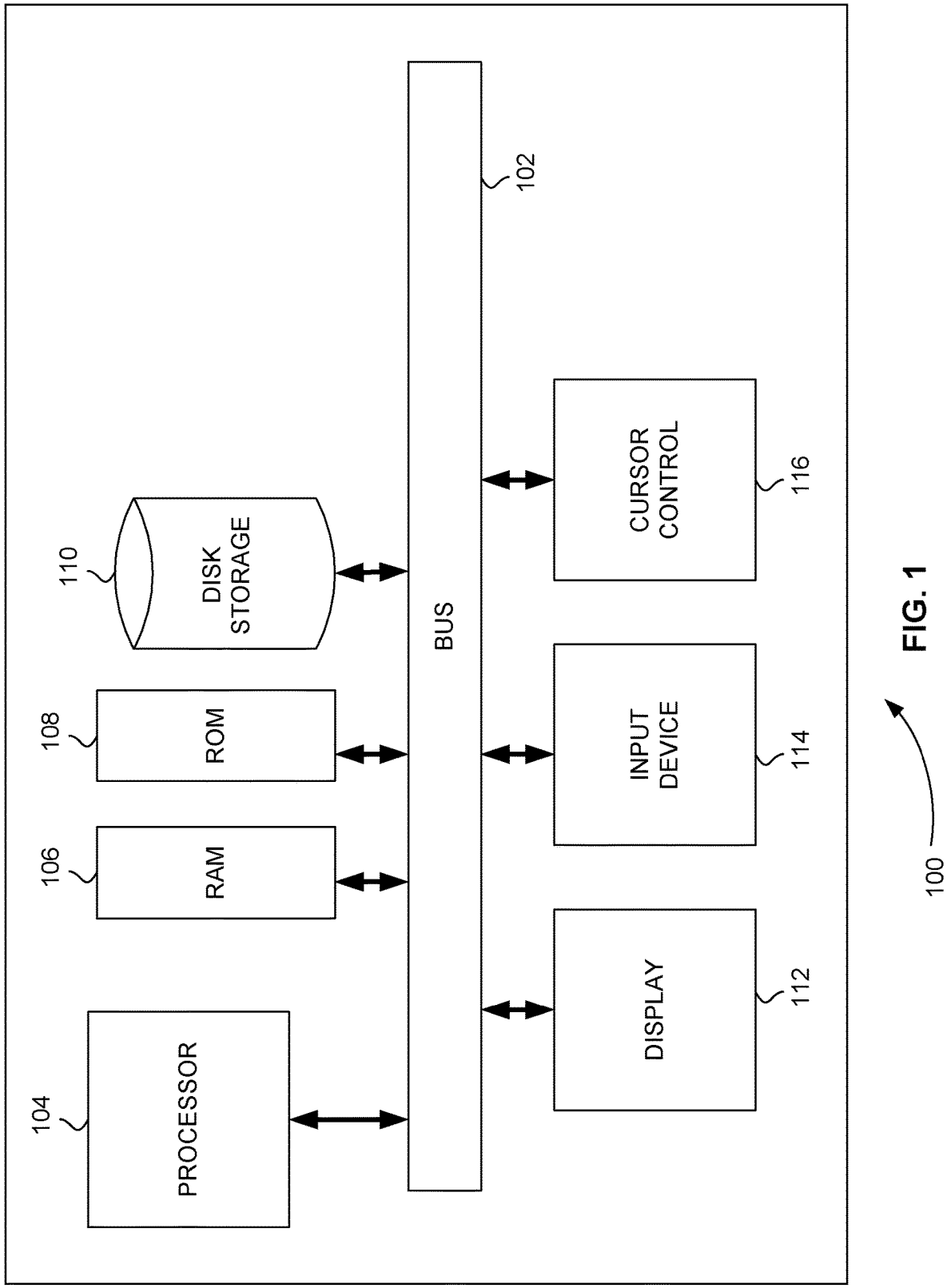
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Detailed Description of a CID and ExD
Dissociation Glycoprotein Analysis Method

Embodiments of systems and methods for operating tandem mass spectrometer to identify a peptide sequence of a glycopeptide of a sample are described in this detailed description of the invention. In this detailed description, for purposes of explanation, numerous specific details are set forth to provide a thorough understanding of embodiments of the present invention. One skilled in the art will appreciate, however, that embodiments of the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of embodiments of the present invention.

As described above, a conventional tandem mass spectrometry protein identification experiment involves digesting at least one protein of a sample into peptides, fragmenting each of the peptides found, and producing a product ion spectrum for each of the peptides. The product ion spectra of the peptides found are then compared to a protein database to identify the protein.

Unfortunately, this method of identification cannot be applied to glycoproteins due to the large number of possible different glycoproteins. In other words, building a glycoprotein database and matching experimental spectra to that database is not practical due to the large number of possible different glycoproteins. This problem is referred to above as the glycan database matching problem.

One proposed method of addressing the glycan database matching problem is to perform the tandem mass spectrometry identification experiment using two or more complementary dissociation techniques. As described above, however, there is currently no practical method of combining the data obtained from using two or more complementary dissociation techniques that completely addresses the glycan database matching problem.

In various embodiments, a method of operating a tandem mass spectrometer to perform a glycoprotein identification experiment using two complementary dissociation techniques and combining the data obtained from using two techniques finally completely addresses the glycan database matching problem. More specifically, a method of operating a tandem mass spectrometer to perform a glycoprotein identification experiment using both collision-induced dissociation (CID) and electron-based dissociation (ExD) addresses the glycan database matching problem. Data from the CID fragmentation is used to produce a list of candidate sequences of the peptide portion of the glycopeptides of a glycoprotein. Data from the ExD fragmentation is compared to the candidate sequences of the list in order to identify the peptide candidate sequences of the experimental glycopeptides. Mass differences between the candidate sequences and the experimental glycopeptides are used to identify the glycan mass of the experimental glycopeptides. From the candidate sequences, the glycans, and the sites of modification of the experiment glycopeptides, the entire glycoprotein is reconstructed.

Figure 2:
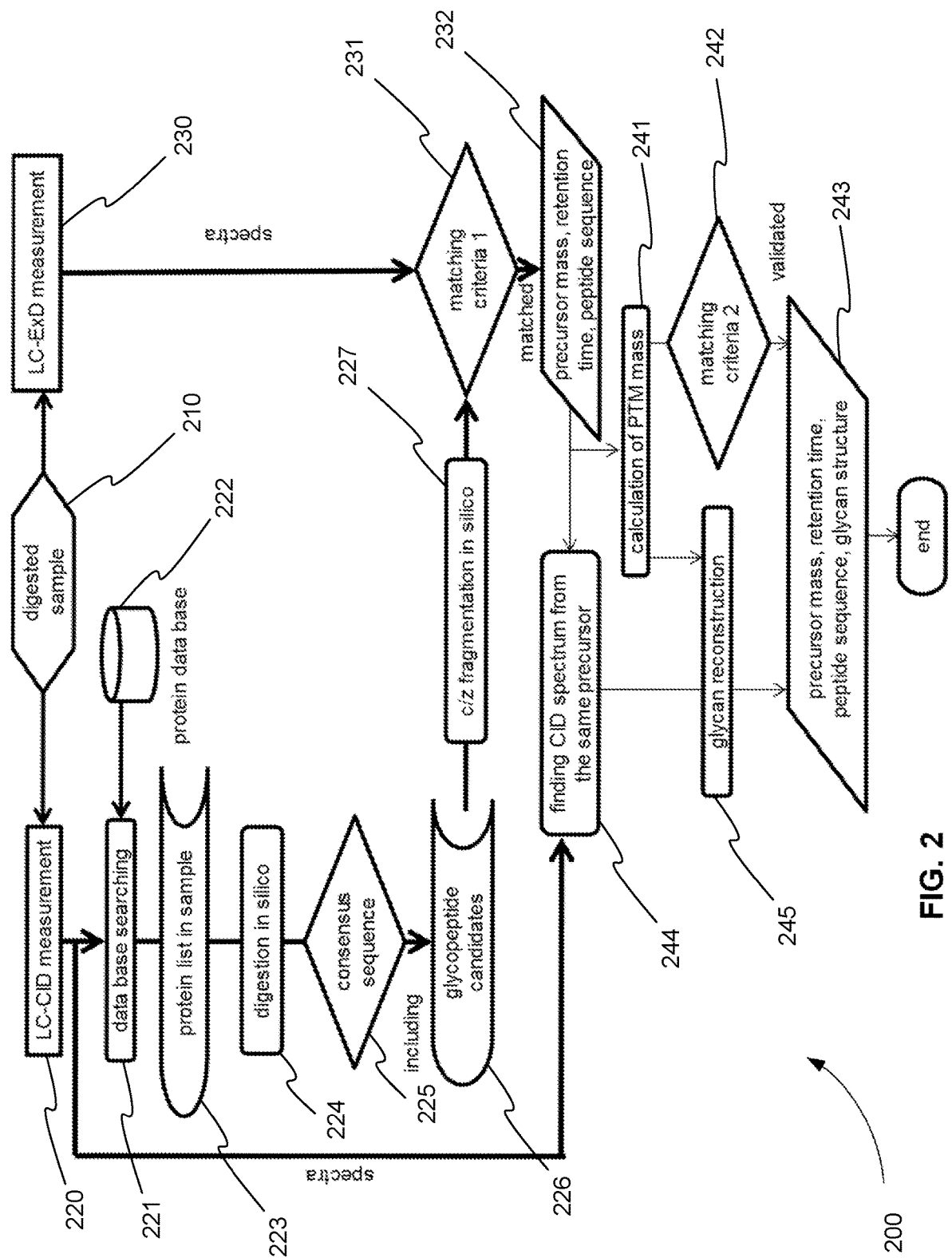
FIG. 2 is an exemplary flowchart showing a method for operating a tandem mass spectrometer to perform glycoprotein identification using both collision-induced dissociation (CID) and electron-based dissociation (ExD) and combining the data obtained from using these two complementary dissociation techniques, in accordance with various embodiments.

FIG. 2 is an exemplary flowchart 200 showing a method for operating a tandem mass spectrometer to perform glycoprotein identification using both CID and ExD and combining the data obtained from using these two complementary dissociation techniques, in accordance with various embodiments. In step 210, one or more glycoproteins of a sample are digested using a protease, for example. The digestion produces one or more glycopeptides for each of the one or more glycoproteins. These glycopeptides are introduced into a tandem mass spectrometer. For example, the glycopeptides are introduced into the tandem mass spectrometer using a liquid chromatography (LC) column and elute from the column and into the tandem mass spectrometer at different retention times.

An ion source of the tandem mass spectrometer ionizes the eluting glycopeptides producing an ion beam of glycopeptide precursor ions. The tandem mass spectrometer analyzes the precursor ions using one of the analysis techniques described above. In an information dependent acquisition (IDA) type method, for example, a precursor ion or mass spectrometry (MS) survey scan is performed to generate a precursor ion peak list. Each of the precursor ions on the peak list is selected and fragmented, producing a product ion spectrum for each precursor ion.

As shown in FIG. 2, in the method for glycoprotein identification, each precursor ion is selected and fragmented in two different mass spectrometry experiments, as described below. In step 220, a precursor ion is fragmented using CID, and the CID product ions are analyzed producing a CID product ion spectrum. In step 230, before or after the experiment of step 220, the same precursor ion is fragmented using ExD, and the ExD product ions are analyzed producing an ExD product ion spectrum.

CID Analysis

As described above, CID dissociates glycans preferentially. As a result, CID produces glycan fragments, which have parts of the glycan or parts of the glycan with entire peptides when CID is applied on the glycopeptides. When CID is applied on unmodified peptides in the samples, it produces peptide fragments, which can be sequenced by comparison to a data base. Glycoproteins produce both glycosylated peptides and unmodified peptides by protease digestion. The glycosylation is intact by the digestion and stay on the digested peptides. The peptide sequence of the glycopeptides and the unmodified peptides are different because they are different portions of a protein.

As a result, and as shown in step 221, the CID product ion spectra of unmodified peptides can be compared to a standard protein database 222. The result of this comparison or database searching is a list of candidate proteins, which includes glycoproteins as well as non glycosylated proteins in the samples as shown in step 223.

In step 224, each candidate protein of the list of candidate proteins found in step 223 is digested in silico. In other words, each candidate protein is fragmented computationally to produce a list of possible peptides. The cleavage rule applied to this computational or theoretical digestion is the same cleavage rule of the actual protease used in step 210.

In various embodiments, a step 225 is performed. In step 225, the list of candidate peptides is amended to include peptides with consensus sequences for N and O glycosylations. As described above, an N glycan is attached to an asparagine residue (N) with consensus sequences asparagine-X-serine, or asparagine-X-threonine, where X can be any amino acid residue except proline. An O glycan is attached to a serine residue (S) or threonine residue (T). There is no additional consensus sequence for O-glycosylations, so single residue S and T consensus sequences are referred to as the consensus sequences for O-glycosylation in this application. If there is available information on known glycosylation patterns on each glycoproteins, such information can also be included.

In step 226, the list of candidate sequences of the peptide part of the candidate glycopeptides is provided.

CID Analysis of Fetuin

Figure 3:
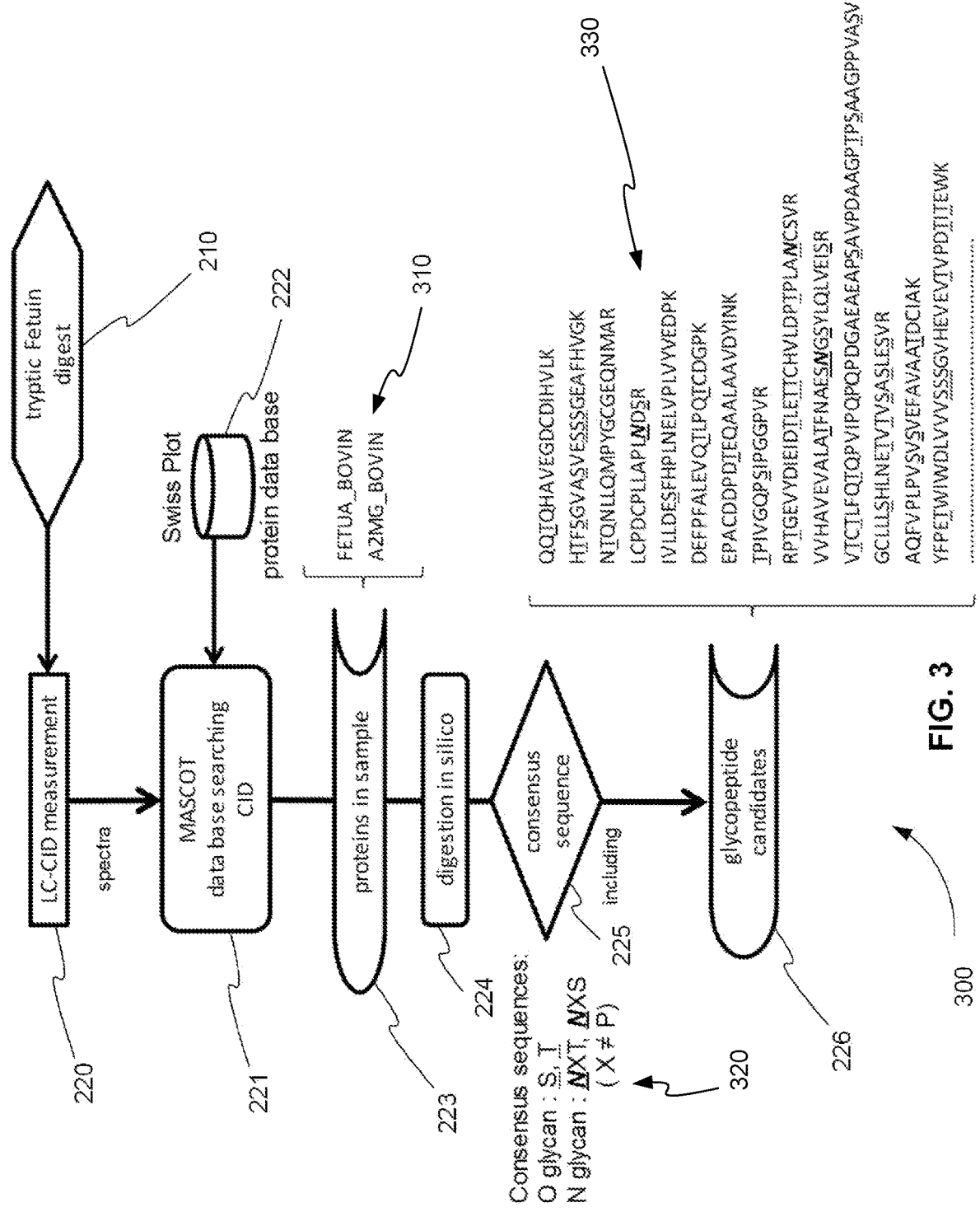
FIG. 3 is an exemplary flowchart showing an example of how the simple glycoprotein Fetuin is processed through the CID analysis part of the method of FIG. 2, in accordance with various embodiments.

FIG. 3 is an exemplary flowchart 300 showing an example of how a glycoprotein, Fetuin, is processed through the CID analysis part of the method of FIG. 2, in accordance with various embodiments. In step 210, Fetuin is digested using trypsin, for example, producing one or more glycopeptides and unmodified peptides. In step 220, the peptides with/without glycans are fragmented using CID, and the CID product ions are analyzed producing a CID product ion spectrum.

As shown in step 221, the CID product ion spectra of Fetuin are compared to a protein database 222, such as Swiss Plot using a data base searching program, such as MASCOT. Here we do not assume the peptides are not glycosylated so that unmodified peptides in the Fetuin digest are identified. This comparison or database searching provides a list of proteins in the samples (both glycosylated and un-glycosylated, and both targets and contaminations) as shown in step 223. The list of candidate proteins 310 identified by the database searching includes FETUA_BOVIN and A2MG_BOVIN, for example.

In step 224, each candidate protein of the list of the including proteins found in step 223 is digested in silico. In other words, each protein is fragmented computationally to produce a list of possible peptides. In the case of use of trypsin, C terminal side of K (lysine) and R (arginine) are mainly cleaved except their neighbor is proline, i.e., xxxKPxx and xxxRPxx cases.

In various embodiments, a step 225 is performed. In step 225, the list of computationally generated candidate peptides is amended to only include peptides with consensus sequences for N and O glycans. These consensus sequences are found using rules 320 for the modification sites of O and N type glycans. For example, O glycan modification sites include S and T residues. N glycan modification sites include NxT and NxS sequences, wherein x is not equal to P.

In step 226, the list of sequences 330 of the peptide part of the candidate glycopeptides is provided. Note that the O glycan modification sites are underlined, and the N glycan modification sites are underlined, italicized, and boldened in the consensus sequences of list 330. List of candidate sequences 330 only includes peptides with N and O glycan consensus sequences because only these candidate sequences were chose in step 225.

ExD Analysis

Returning to FIG. 2, in step 230, the same precursor ion (digested from the sample) that was fragmented with CID is also fragmented using ExD, and the ExD product ions are analyzed producing an ExD product ion spectrum. As described above, ExD dissociates peptide backbones preferentially and the glycans stay on the peptide fragments intact, so it is an ideal tool to analyze peptide sequences. In other words, the ExD product ion spectrum is particularly well suited for determining the glycosylated amino acid residues.

As a result, in step 231, the ExD product ion spectrum is compared to the computationally determined product ions of the candidate sequences to determine the peptide part of a glycopeptide. The peptide candidates found in step 226 are fragmented in silico in step 227 according to the ExD dissociation rules, which produces c and z fragments. In the case that ECD by low electron energy (0—ca 3 eV), N terminal side of proline is not cleaved as an exception. In the case that hot ECD by higher electron energy (>3 eV), N terminal side of proline is also cleaved. The resulting theoretical c and z product ion candidate sequences are then converted to m/z values. These m/z values are finally compared in step 231 to the measured m/z values of the product ions of the ExD product ion spectrum.

More specifically, each ExD spectrum contains fragment or product ion peaks, and the fragment types are c (N terminal fragments) and z (C terminal fragments). The experimentally obtained mass-to-charge ratios (m/z) of the product ion peaks are compared to calculated m/z values of the theoretically calculated candidate fragment sequences in step 227. To evaluate the degree of matching, a "score" is calculated for each candidate peptide sequence calculated in step 226. A higher score means better matching in this example.

Many scoring policies are possible. Such scoring policies may be for peptides in general and not just for glycopeptides. These scoring methods can be referred to as peptide scoring. For example, a peptide score may be calculated for each candidate peptide sequence based on how well the experimentally obtained m/z values of the product ion peaks compare to the calculated m/z values of the theoretically calculated candidate fragment sequences.

In various embodiments and for glycopeptides, in particular, each candidate peptide sequence calculated in step 226 is scored based on c fragments matching the N terminal side of the candidate peptide sequence and z fragments matching the C terminal side of the candidate peptide sequence up to the consensus sequence glycosylation modification site because the mass of glycosylation is not known, which is attached on the amino acid residue that satisfies the consensus sequence rule. This score can be referred to as an initial peptide score.

Based on the added glycopeptide scoring provided in step 231, a score is determined for each candidate peptide sequence that was calculated in step 226. The candidate peptide with the highest score above some predetermined minimum threshold is identified as a glycopeptide of the sample in step 232. The precursor ion m/z and charge, retention time, and peptide sequence of the candidate peptide with the highest score are also determined in step 232.

ExD Analysis of Fetuin

Figure 4:
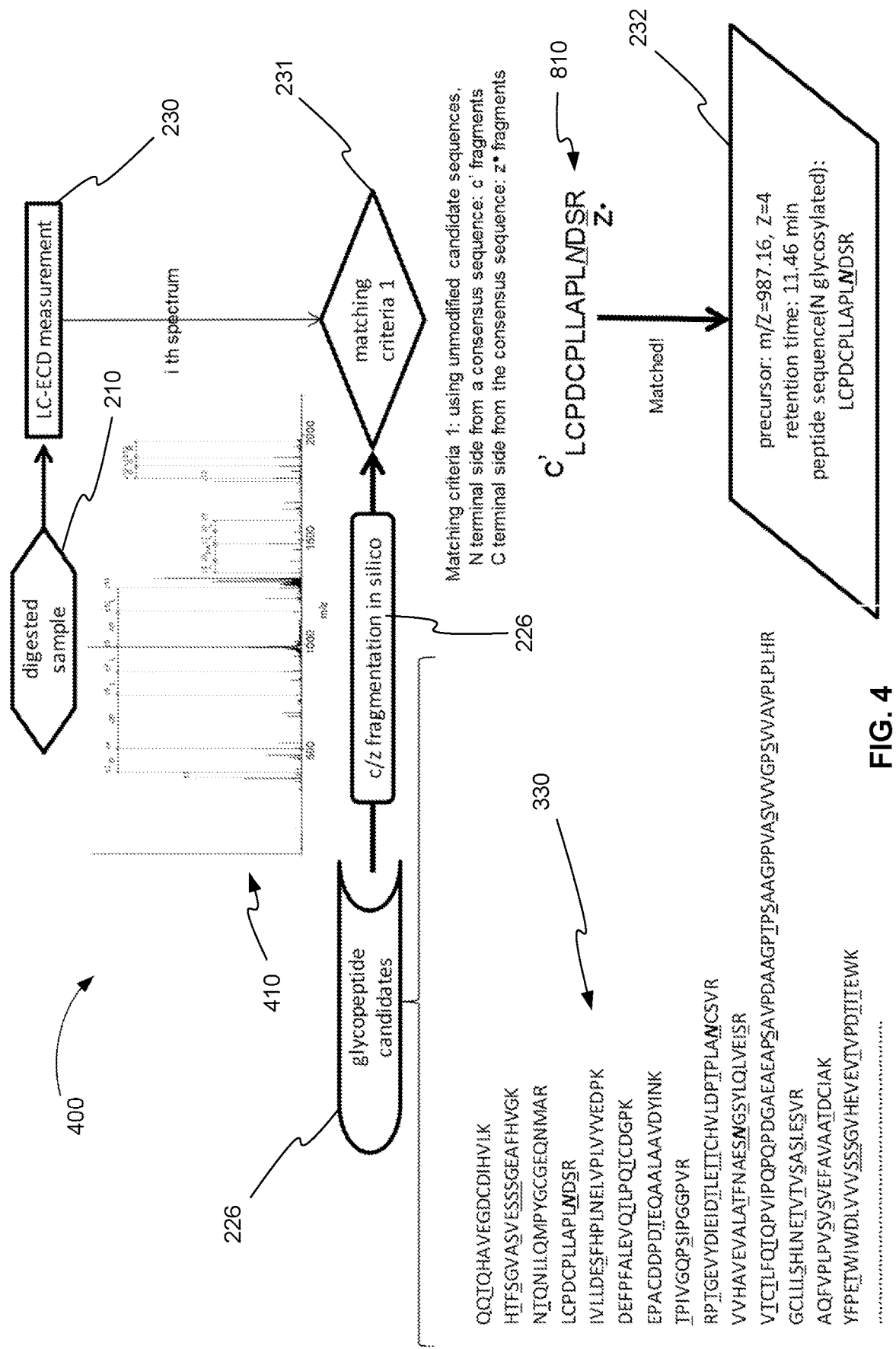
FIG. 4 is an exemplary flowchart showing an example of how the simple glycoprotein Fetuin is processed through the ExD analysis part of the method of FIG. 2, in accordance with various embodiments.

FIG. 4 is an exemplary flowchart 400 showing an example of how the Fetuin digest is processed through the ExD analysis part of the method of FIG. 2, in accordance with various embodiments. In step 210, Fetuin is digested using trypsin, for example, producing one or more glycopeptides. In step 230, the same glycopeptides in the digested fetuin that were targeted in the CID measurement are fragmented using ExD, and the ExD product ions are analyzed producing an ExD product ion spectrum 410.

In various embodiments, in step 230, glycopeptides of Fetuin are eluted from a liquid chromatography (LC) column, for example. As a result, an ExD product ion spectrum 410 is one of many ExD product ion spectra obtained for the glycopeptides of Fetuin.

Figure 5:
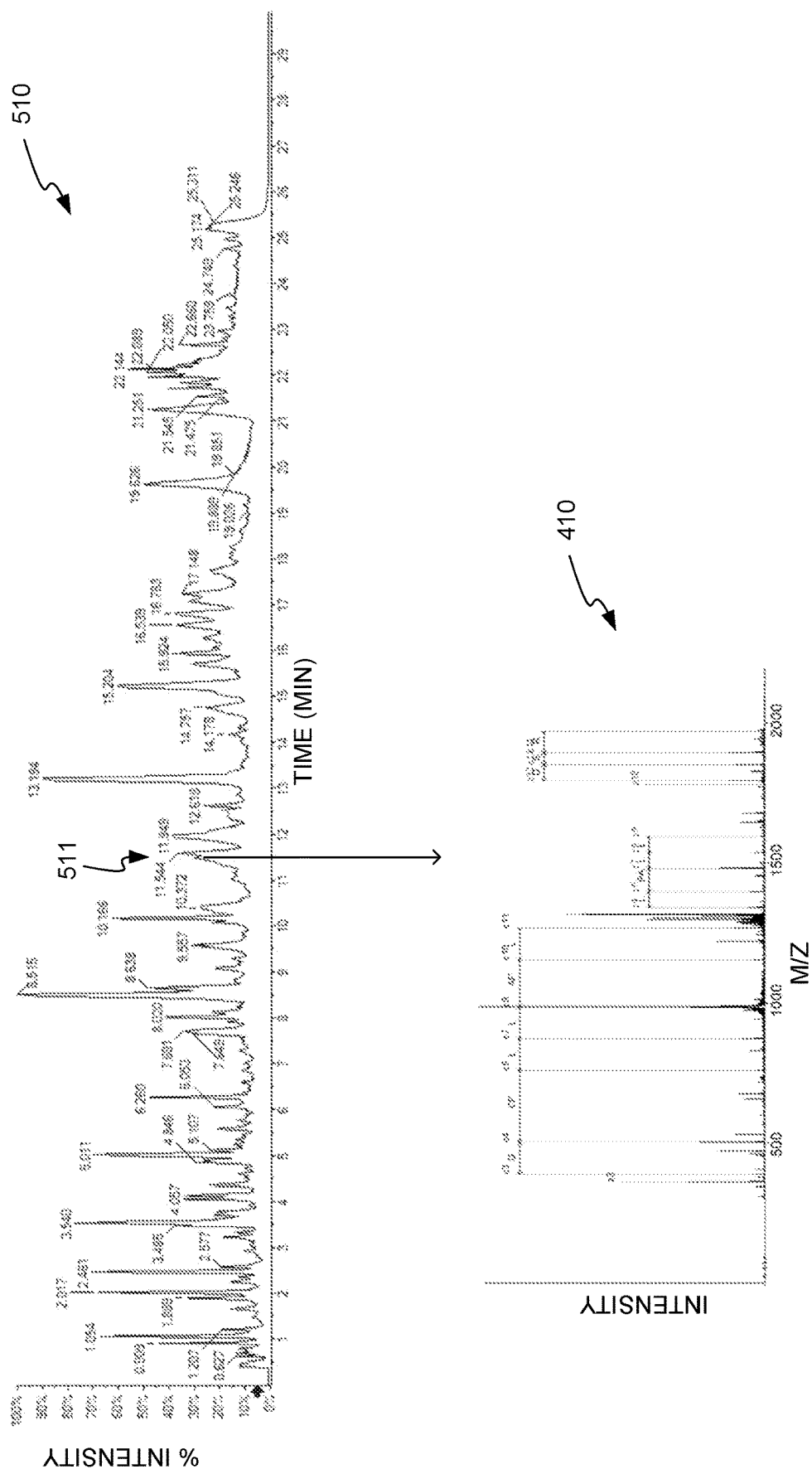
FIG. 5 is an exemplary collection of mass spectrometry measurements taken from the elution of the glycopeptides of Fetuin, in accordance with various embodiments.

FIG. 5 is an exemplary collection 500 of mass spectrometry measurements taken from the elution of the glycopeptides of Fetuin, in accordance with various embodiments. Plot 510, for example, is a plot of the MS or precursor ion chromatogram of the glycopeptides of Fetuin. Plot 510 shows the intensity of the precursor ions of the glycopeptides of Fetuin measured over time. Chromatographic peaks of the precursor ions of the glycopeptides of Fetuin indicate the retention time of specific glycopeptides. For example, precursor ion peak 511 has a retention time of about 11.46 min.

In addition, at or near the precursor ion peaks of the glycopeptides of Fetuin the precursor ions are selected and fragmented using tandem mass spectrometry or MS/MS. As described in reference to FIG. 2, this tandem mass spectrometry is performed using both CID and ExD fragmentation. Plot 410, for example, shows the product ion spectrum from an ExD fragmentation for the precursor ion present at time 11.46 min.

Returning to FIG. 4, the product ion spectrum in plot 410, for example, is used to determine the peptide part of a glycopeptide in step 231. Recall that list of candidate sequences 330 of the peptide part of the candidate glycopeptides of Fetuin were previously found in step 226 from the CID fragmentation. These candidate sequences 330 were further fragmented in silico or computationally in step 227 according to the rules known for c and z fragmentation.

In step 231, the theoretical c and z product ion m/z values calculated in step 227 are compared to the measured m/z values of the product ions of ExD product ion spectrum 410. As described above, this comparison is scored to determine the matching glycopeptide.

Glycopeptide Scoring

More specifically, the glycopeptide scoring starts by determining if the candidate peptide sequence does not contain a consensus sequence for a modification site of a glycopeptide. If the candidate peptide sequence does not contain a consensus sequence, the final score is set to zero. In other words, the candidate peptide sequence is neglected. Note that this step is the same as step 225 of FIG. 2. It is, therefore, not needed if step 225 is performed. Recall that step 225 makes sure that each candidate peptide sequence includes a consensus sequence for a glycosylation modification site.

If each candidate peptide sequence includes a consensus sequence, four steps are performed for each candidate peptide sequence. 1. Increment the score of the candidate peptide sequence, for each m/z value of a product ion peak of the ExD product ion spectrum 410 that matches to an m/z value of a c fragment of the plurality of theoretical fragments from the N terminal side of the sequence to a consensus sequence of a glycan modification site. 2. Do not increment the score of the candidate peptide sequence, for each m/z value of a product ion peak of the ExD product ion spectrum 410 that matches to an m/z value of a z fragment of the plurality of theoretical fragments from the N terminal side of the sequence to a consensus sequence of a glycan modification site. 3. Do not increment the score of the candidate peptide sequence, for each m/z value of a product ion peak of the ExD product ion spectrum 410 that matches to an m/z value of a c fragment of the plurality of theoretical fragments from the C terminal side of the sequence to a consensus sequence of a glycan modification site, and 4. Increment the score of the candidate peptide sequence, for each m/z value of a product ion peak of the ExD product ion spectrum 410 that matches to an m/z value of a z fragment of the plurality of theoretical fragments from the C terminal side of the sequence to a consensus sequence of a glycan modification site.

These four steps essentially attempt to match c fragments from the N terminal side up to a glycosylation modification site and z fragments from the C terminal side up to a glycosylation modification site. If these types of matches are made, the score is increased. If any other matches of c or z fragments are made, the score is not increased. Matches are made only up to the glycosylation modification site because the glycan remains attached to the peptide at the modification site and the fragments will not match beyond the modification site.

Figure 6:
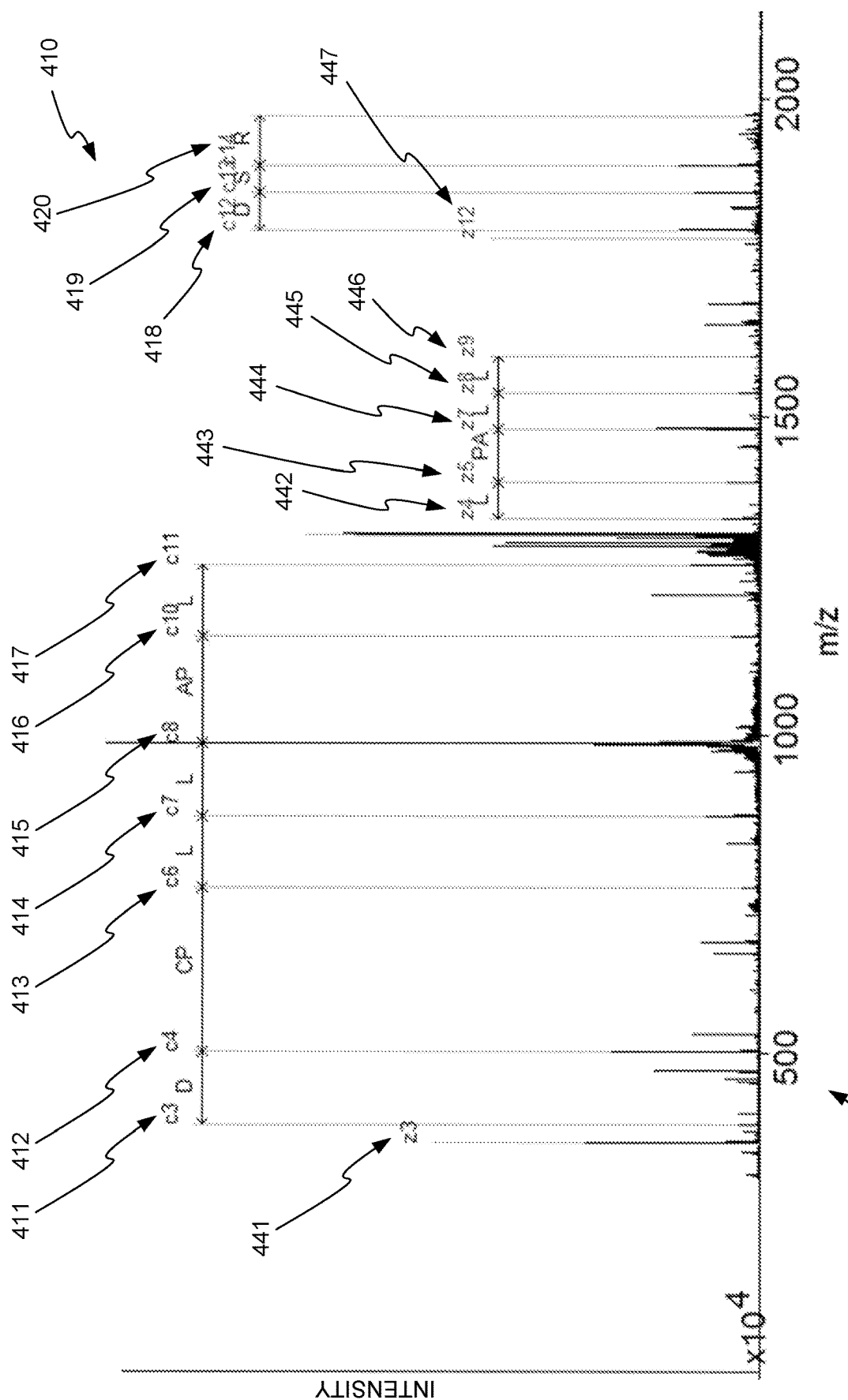
FIG. 6 is an exemplary diagram showing the comparison of measured m/z values of the product ions of an ExD product ion spectrum to the theoretical c and z product ion m/z values of a candidate peptide sequence, in accordance with various embodiments.

FIG. 6 is an exemplary diagram 600 showing an ExD product ion spectrum of a glycopeptide, in accordance with various embodiments.

Figure 8:
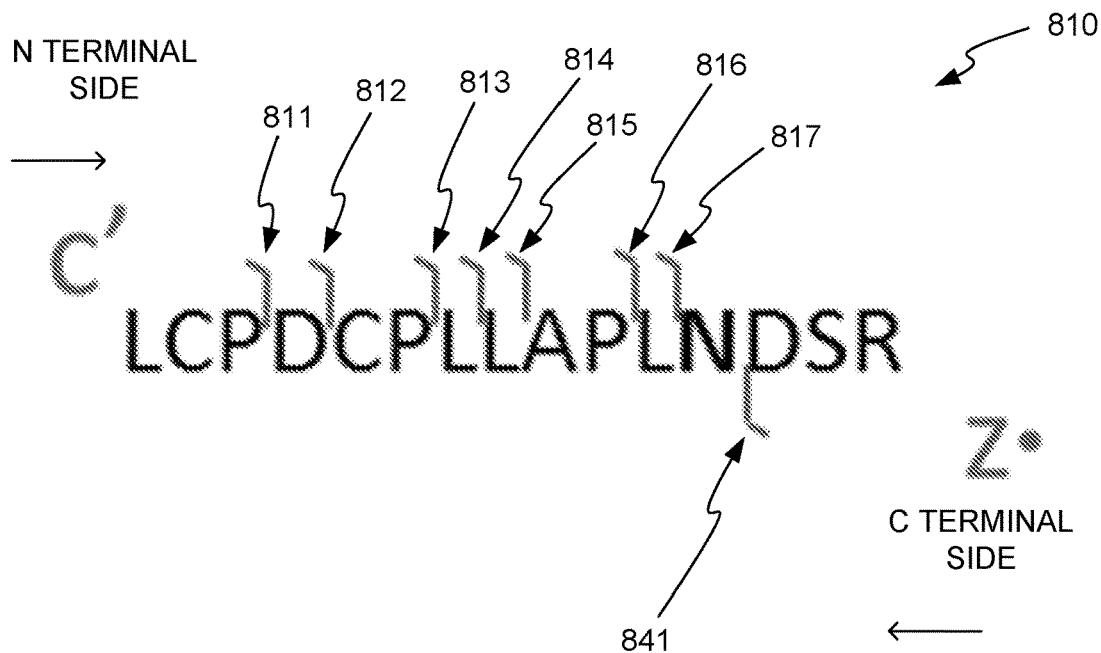
FIG. 8 is an exemplary diagram showing the comparison of measured m/z values of the product ions of an ExD product ion spectrum to the theoretical c and z product ion m/z values of a candidate peptide sequence that can include the PTM mass, in accordance with various embodiments.
Figure 8:
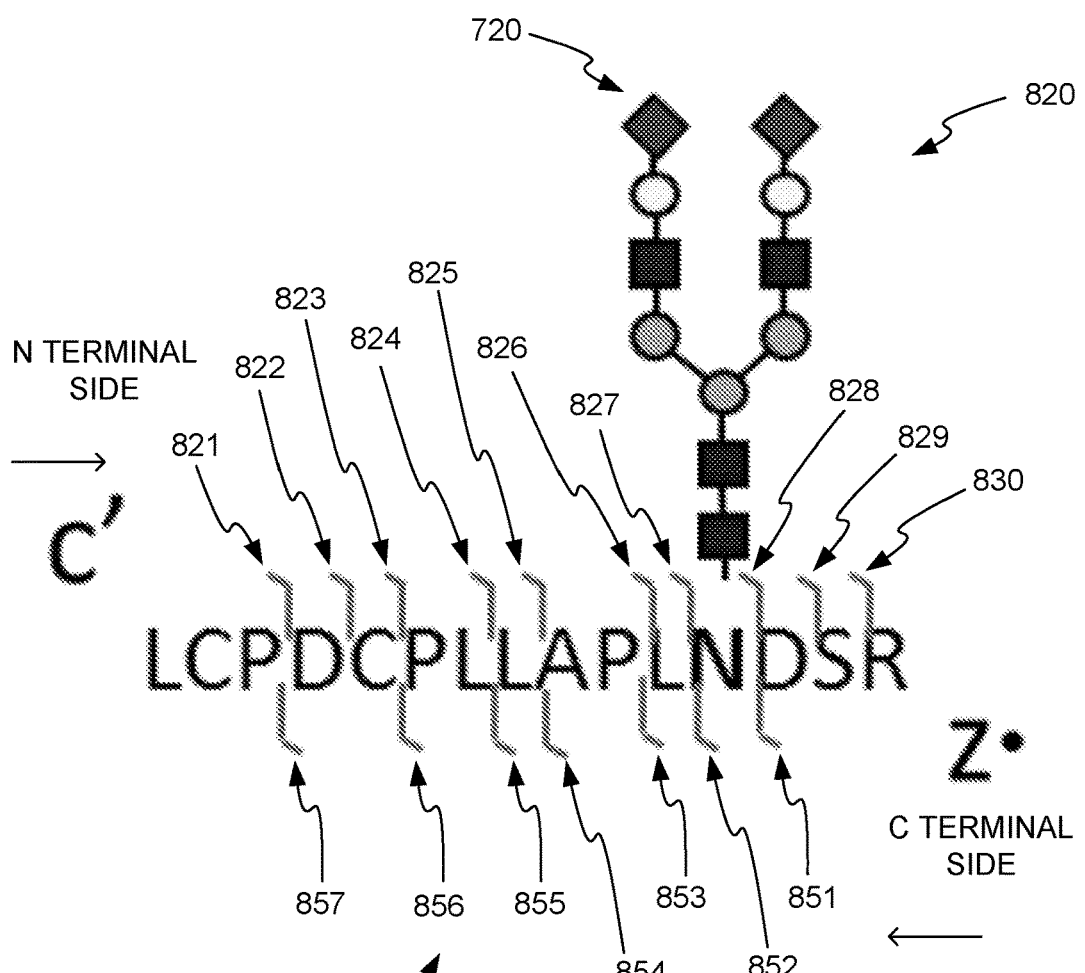

FIG. 8 is an exemplary diagram 800 showing theoretical c and z product ion m/z values of a candidate glycopeptide sequence with and without an attached glycan, in accordance with various embodiments.

In various embodiments, ExD product ion spectrum 410 of FIG. 6 is compared to candidate glycopeptide sequence 810 of FIG. 8, which is the sequence without an attached glycan. Note that the structure and mass of the glycan at the possible modification site (i.e., N) is unknown at this time. Fixed modifications, such as carbamidomethylation at cysteine, should be included in the candidate sequences.

As described above, the comparison scoring starts by determining if candidate glycopeptide sequence 810 of FIG. 8 does not contain a consensus sequence for a glycosylation modification site. Recall that O glycan modification sites include S and T residues. N glycan modification sites include NxT and NxS sequences, wherein x is not equal to P. As a result, candidate glycopeptide sequence 810 does indeed include a consensus sequence. For example, candidate glycopeptide sequence 810 includes the consensus sequence NDS for an N glycan and the consensus sequence S for an O glycan.

The four glycopeptide scoring steps described above are applied to one or more of the experimentally obtained m/z values of the product ion peaks of ExD product ion spectrum 410 of FIG. 6. For example, the four glycopeptide scoring steps described above are applied to one or more m/z values of the product ion peaks of ExD product ion spectrum 410.

In regard to glycopeptide scoring step 1, the m/z values of product ion peaks 411, 412, 413, 414, 415, 416, and 417 of ExD product ion spectrum 410 of FIG. 6 match the m/z values of theoretical fragments 811, 812, 813, 814, 815, 816, and 817 of candidate glycopeptide sequence 810 of FIG. 8, respectively. Theoretical fragments 811, 812, 813, 814, 815, 816, and 817 of candidate glycopeptide sequence 810 are c fragments from the N terminal side of candidate glycopeptide sequence 810. They are also fragments before a consensus sequence location (NDS). As a result, the m/z values of product ion peaks 411, 412, 413, 414, 415, 416, and 417 of ExD product ion spectrum 410 of FIG. 6 meet the condition of step 1 for candidate glycopeptide sequence 810 of FIG. 8. As a result, the score of candidate glycopeptide sequence 810 is incremented by a predetermined value (giving a higher score) for each match.

The score of candidate glycopeptide sequence 810 of FIG. 8 is not increased for any matches made in scoring steps 2 or 3.

Candidate glycopeptide sequence 810 of FIG. 8 does, however, meet the condition of glycopeptide scoring step 4. Candidate glycopeptide sequence 810 does include a z fragment (fragment 841) from the C terminal side. In addition, this fragment is before the consensus sequence NDS. The m/z value of fragment 841 also matches the m/z value of product ion peak 441 of ExD product ion spectrum 410 of FIG. 6. As a result, the score of candidate glycopeptide sequence 810 of FIG. 8 is again incremented by a predetermined value (giving a higher score).

Returning to FIG. 4, in step 231, candidate glycopeptide sequence 810 of list of candidate sequences 330 is found to match ExD product ion spectrum 410 with the highest score. As a result, in step 232, candidate glycopeptide sequence 810 is identified as a glycopeptide of the sample. In various embodiments, in step 232, the m/z, charge, and retention time of the glycopeptide is determined from the experimental MS or precursor ion measurement as described in reference to FIG. 5, for example. The peptide sequence determined in step 232 is known from the candidate peptide sequence.

What remains unknown at step 232 is the actual modification site of the peptide in the case that the candidate peptide sequence has multiple consensus sequences. Also unknown at step 232 is the structure of the glycan.

Validation, Modification Site Identification, and Glycan Reconstruction

Returning to FIG. 2, additional steps can be performed to verify the sequence of the peptide part of the glycopeptide, identify the actual modification site of the peptide part of the glycopeptide, and determine the structure of the glycan part of the glycopeptide. In step 241, the mass of the glycan or the post-translational modification (PTM) mass is calculated. The PTM mass is calculated from the mass difference between the measured precursor ion and the theoretical mass of the candidate peptide sequence.

In step 242, in order to validate the sequence and identify the actual modification site of the peptide part of the glycopeptide, the PTM mass is theoretically added to the modification sites given by the consensus sequence of the candidate sequence found in step 232. The candidate sequence is then scored again by comparing modified candidate sequence theoretical fragments to measured ExD fragments. If the score is improved due to the addition of the PTM mass to theoretical fragments, then the candidate sequence is validated and again identified in step 243. The modification site is also determined by this comparison and identified in step 243.

In order to determine the structure of the glycan, in step 244, the CID product ion spectrum corresponding to the ExD product ion spectrum is found using the m/z, charge, and retention time of the precursor ion of the glycopeptide found in step 232. From the CID product ion spectrum glycan fragments are found. From these glycan fragments and the PTM mass found in step 241, the glycan is reconstructed in step 245. In step 243 the glycan structure is reported.

Fetuin Validation, Modification Site Identification, and Glycan Reconstruction

Figure 7:
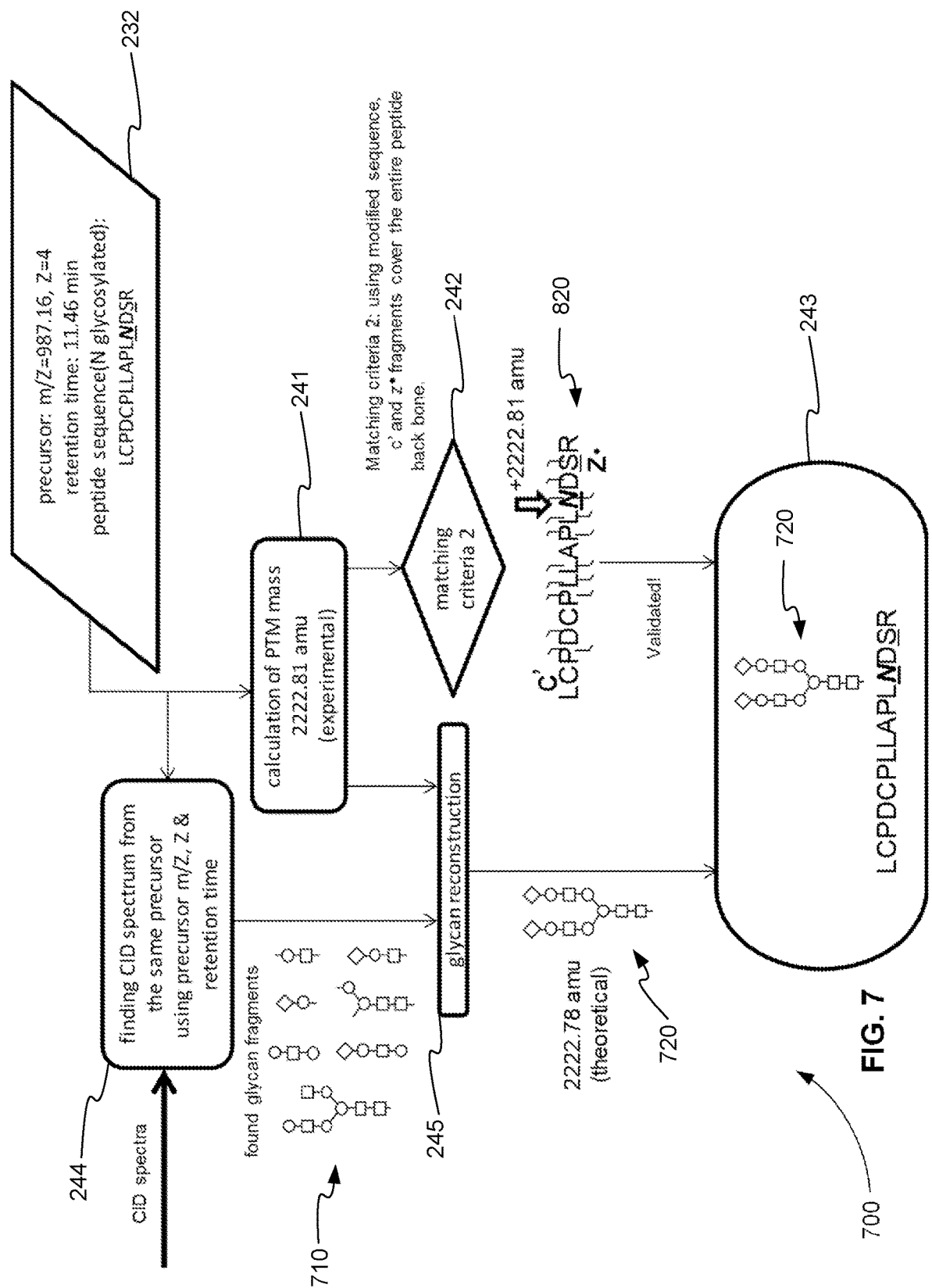
FIG. 7 is an exemplary flowchart showing an example of how the sequence of the peptide part of a glycopeptide of the simple glycoprotein Fetuin is validated, how the actual modification site of the peptide part of the glycopeptide is identified, and how the structure of the glycan part of the glycopeptide is determined using the method of FIG. 2, in accordance with various embodiments.

FIG. 7 is an exemplary flowchart 700 showing an example of how the sequence of the peptide part of a glycopeptide of Fetuin is validated, how the actual modification site of the peptide part of the glycopeptide is identified, and how the structure of the glycan part of the glycopeptide is determined using the method of FIG. 2, in accordance with various embodiments. In step 241, the PTM mass is calculated. The PTM or glycan mass is found by subtracting the theoretical mass of the candidate peptide sequence found in step 232 from the experimental mass (m/z×z) of the precursor ion found in step 232. For example, a PTM mass of 2222.81 amu is found in step 241 for the glycopeptide of Fetuin by subtracting the theoretical mass of the candidate sequence found in step 232 from the experimental mass (987.16×4) of the precursor ion found in step 232.

In step 242, the PTM mass is used to score the candidate peptide sequence. This additional scoring includes four steps. (1) The PTM mass is added to each of glycosylation modification sites (N, S, and T) of consensus sequences of theoretical fragments of the candidate peptide sequence, producing additional theoretical fragments. (2) The experimentally obtained m/z values of the product ion peaks of the ExD product ion spectrum are again compared to the m/z values of the theoretical fragments of the candidate peptide sequence including the m/z values of the additional theoretical fragments now including the PTM mass. (3) Now, for one or more of the product ion peaks of the ExD product ion spectrum, when each product ion peak matches to a theoretical m/z of a c fragment of the entire candidate peptide sequence, the score is incremented (given a higher score). Similarly, for one or more of the product ion peaks of the ExD product ion spectrum, when each product ion peak matches to a theoretical m/z of a z fragment of the entire candidate peptide sequence, the score is incremented (given a higher score). (4) If the score of the candidate peptide sequence is now higher than before, then the candidate peptide sequence and the PTM mass are validated. Additionally, if a product ion peak matches to a theoretical m/z fragment that includes the PTM mass at a particular modification site, then the modification site of the candidate peptide sequence is found.

Returning to FIG. 8, (1) if the PTM mass is added to each of glycosylation modification sites (N, S, and T) of consensus sequences of theoretical fragments of the candidate peptide sequence, candidate glycopeptide sequence 820 now includes the PTM (glycan 720) at modification site N of the consensus sequence NDS. (2) The experimentally obtained m/z values of the product ion peaks of ExD product ion spectrum 410 of FIG. 6, for example, are again compared to the m/z values of the theoretical fragments of now candidate peptide sequence 820 of FIG. 8 including the m/z values of the additional theoretical fragments now including the PTM mass.

As a result, (3) now when the m/z values of the product ion peaks of ExD product ion spectrum 410 of FIG. 6 are matched to the theoretical fragments of candidate peptide sequence 820 of FIG. 8, there are more matches. For example, from the N terminal side the m/z values of product ion peaks 411, 412, 413, 414, 415, 416, and 417 of ExD product ion spectrum 410 of FIG. 6 still match the m/z values of theoretical fragments 821, 822, 823, 824, 825, 826, and 827 of candidate glycopeptide sequence 820 of FIG. 8, respectively. However, now m/z values of product ion peaks 418, 419, and 420 of ExD product ion spectrum 410 of FIG. 6 additionally match the m/z values of theoretical fragments 821, 822, 823, 824, 825, 826, and 827 of candidate glycopeptide sequence 820 of FIG. 8, respectively.

Similarly, from the C terminal side the m/z value of product ion peak 441 of ExD product ion spectrum 410 of FIG. 6 still matches the m/z value of theoretical fragment 851 of candidate glycopeptide sequence 820 of FIG. 8. However, now m/z values of product ion peaks 442, 443, 444, 445, 446, and 447 of ExD product ion spectrum 410 of FIG. 6 additionally match the m/z values of theoretical fragments 852, 853, 854, 855, 856, and 857 of candidate glycopeptide sequence 820 of FIG. 8, respectively. As a result, the score of candidate glycopeptide sequence 820 is again incremented (given a higher score) for each match. Note that this scoring does not depend on whether or not the fragments are from the N terminal side or the C terminal side.

(4) Since the score of candidate glycopeptide sequence 820 is now higher than before, candidate glycopeptide sequence 820 and the PTM mass are validated. Additionally, since experimental product ion peaks matched to theoretical m/z fragments that included the PTM mass at modification site N of the consensus sequence NDS, the modification site off candidate glycopeptide sequence 820 is identified as site N of the consensus sequence NDS.

Returning to FIG. 7, the matching of candidate glycopeptide sequence 820 with the PTM mass attached in step 242 results in the validation of candidate glycopeptide sequence 820 in step 243. In addition, through this matching in step 242 the modification site is identified as site N of the consensus sequence NDS in step 243.

Glycan Structure Reconstruction

The structure of the glycan 720 at the modification site is also shown in step 243. In various embodiments, the glycan structure 720 is found from the PTM mass calculated in step 241. In one embodiment, using the PTM mass, glycan structure 720 is estimated using one or more glycan databases. For example, glycan structure 720 is found by finding a glycan in the one or more glycan databases that has a glycan mass within a predetermined mass threshold of the experimental PTM mass.

In another embodiment, using the PTM mass, Using the PTM mass calculated in the previous claim, glycan structure 720 is estimated by finding a matching mass from any combination of a list of component sugars. This list of component sugars can include, but is not limited to, Gal, Man, GlcNAC, GalNAc, Fuc, Neu5Gc, and Neu5Ac.

In various embodiments, the glycan structure 720 is found from the PTM mass calculated in step 241 and from glycan fragments appearing in the CID product ion spectrum. The CID product ion spectrum corresponding to the ExD product ion spectrum is found in step 244 using the m/z, charge, and retention time of the precursor ion of the glycopeptide found in step 232. From the CID product ion spectrum glycan fragments 710 are found. In one embodiment, from glycan fragments 710 and the experimental PTM mass found in step 241, theoretical glycan structure 720 is found in step 245 and reported in step 243.

In another embodiment, using glycan fragments 710 and the experimental PTM mass found in step 241, an appropriate glycan structure is estimated using one or more glycan databases. For example, glycan structure 720 is found in step 245 by finding a glycan in the one or more glycan databases that has a glycan mass within a predetermined mass threshold of the experimental PTM mass and that has subunits matching glycan fragments 710.

FIGS. 2-8 describe methods for identifying at least one glycopeptide of a sample. It is well known to one of ordinary skill in the art that a glycoprotein can be identified from one or more glycopeptides. In other words, the steps described above can be performed iteratively to find two or more glycopeptides in order to identify a glycoprotein.

CID and ExD Sample Introduction and Analysis Methods

Returning to FIG. 2, in various embodiments, the LC-CID measurement performed in step 220 and the LC-ExD measurement performed in step 230 are performed separately for the same sample. In other words, the measurements performed in steps 220 and 230 are separate mass spectrometry experiments performed on the same digested sample 210. The separate CID and ExD mass spectrometry experiments in steps 220 and 230 can each use a conventional IDA tandem mass spectrometry workflow, for example.

Figure 9:
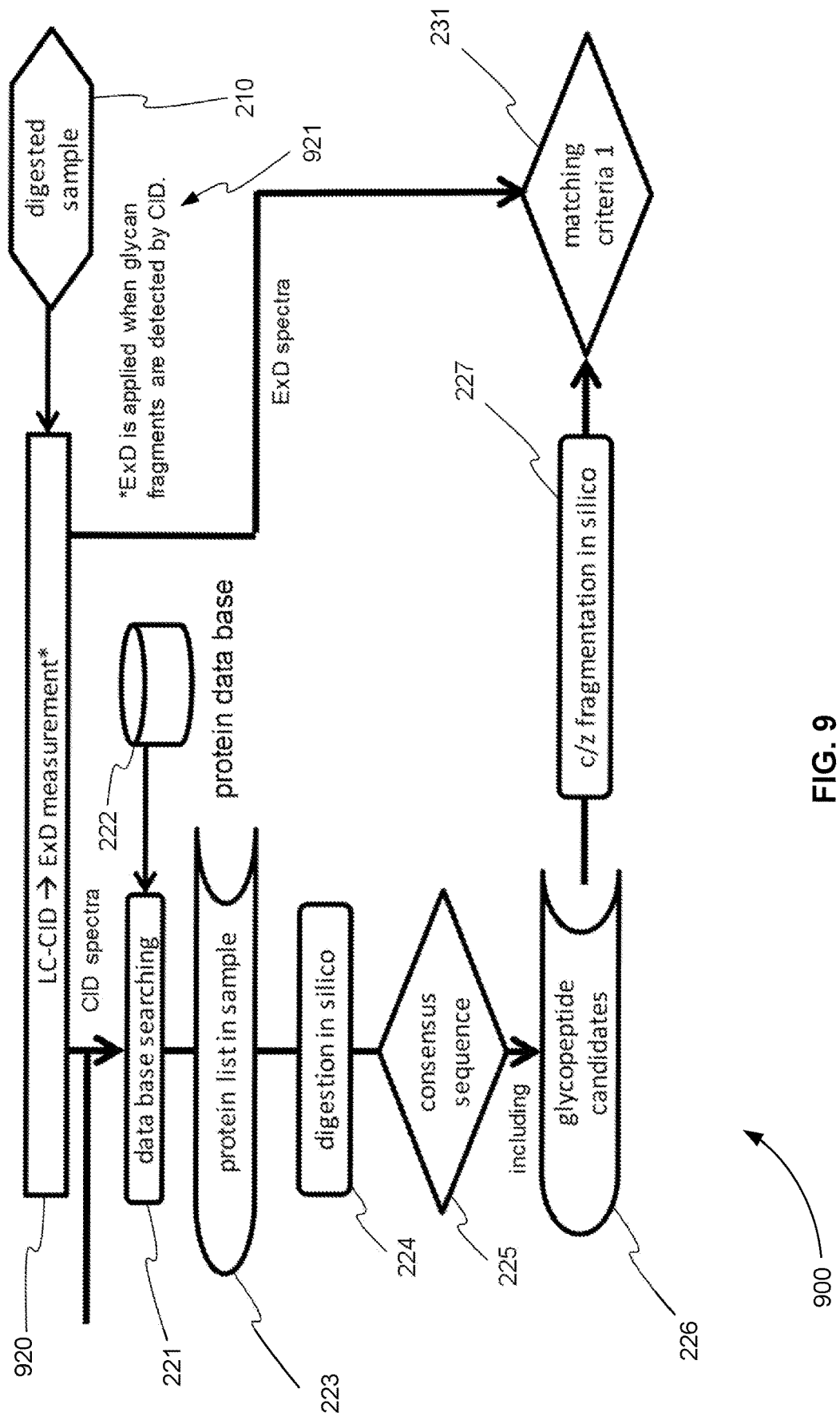
FIG. 9 is an exemplary flowchart showing the initial steps of a method for operating a tandem mass spectrometer to perform glycoprotein identification using both CID and ExD, where CID and ExD analysis is performed in a single mass spectrometry experiment, in accordance with various embodiments.

FIG. 9 is an exemplary flowchart 900 showing the initial steps of a method for operating a tandem mass spectrometer to perform glycoprotein identification using both CID and ExD, where CID and ExD analysis is performed in a single liquid chromatograph-mass spectrometry (LC-MSMS) experiment, in accordance with various embodiments. In step 210, one or more glycoproteins of a sample are digested using proteases, for example.

In step 920, the CID and ExD analysis of the digested sample glycopeptides are performed in a single mass spectrometry experiment. In various embodiments, a precursor ion of a glycopeptide is selected and fragmented using CID. The CID product ions are analyzed producing a CID product ion spectrum. As described in notation 921, if glycan fragments are detected in the CID product ion spectrum, the same precursor ion is selected again and fragmented using and ExD fragmentation in the same LC-MSMS experiment. In order to perform such an ExD analysis triggered by a CID analysis in the same mass spectrometry experiment, a conventional IDA tandem mass spectrometry workflow is modified, for example.

The remaining steps 221, 222, 223, 224, 225, 226, 227, and 231 perform the same functions as described with regard to FIG. 2. The other steps of FIG. 2, except for steps 220 and 230, can be performed using the method of FIG. 9. In other words, step 910 of FIG. 9 replaces steps 220 and 230 of FIG. 2.

Figure 10:
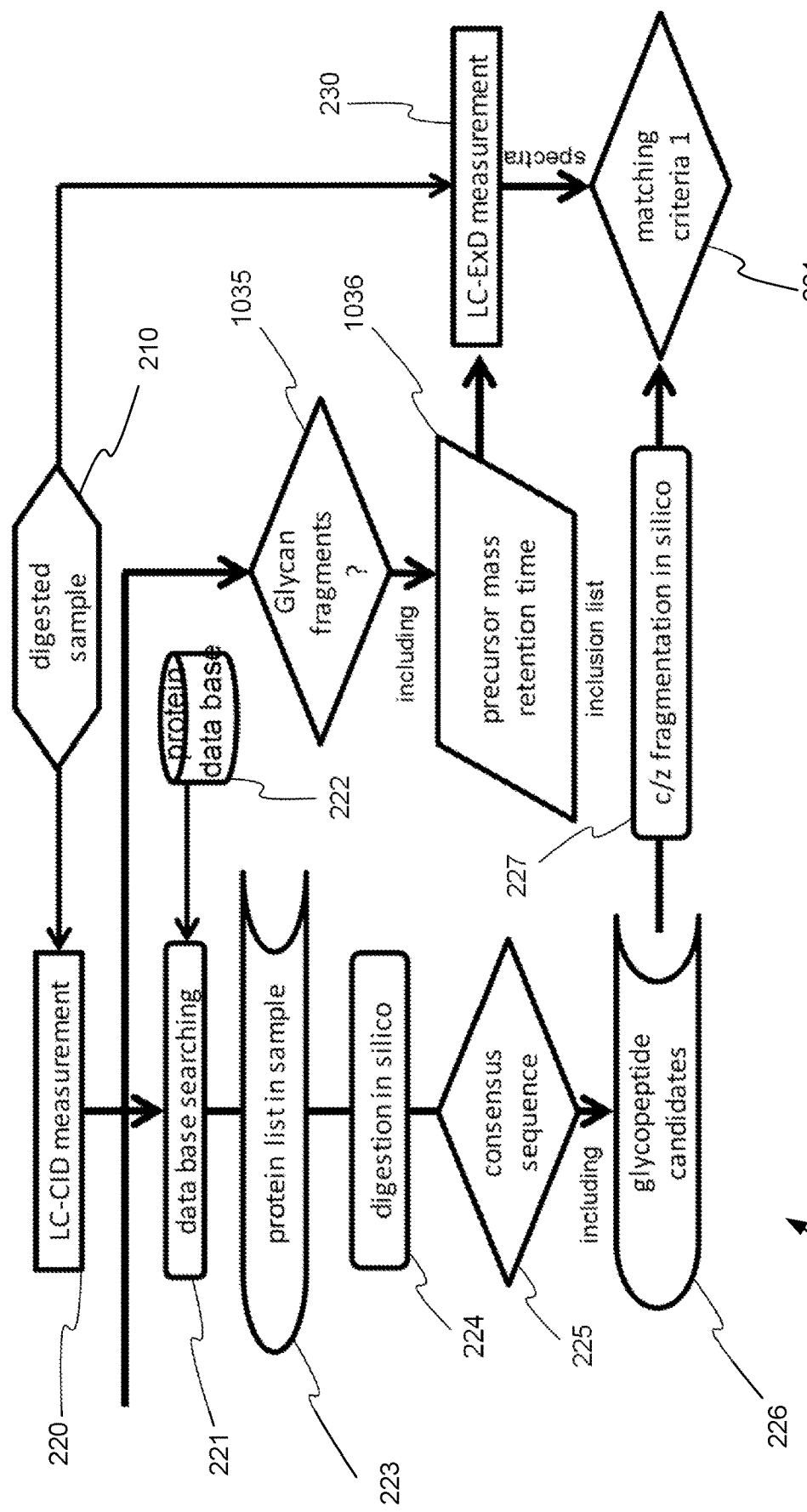
FIG. 10 is an exemplary flowchart showing the initial steps of a method for operating a tandem mass spectrometer to perform glycoprotein identification using both CID and ExD, where CID and ExD analysis are performed in separate mass spectrometry experiments and the ExD analysis of precursor ions is based on finding glycan fragments in the CID analysis, in accordance with various embodiments.

FIG. 10 is an exemplary flowchart 1000 showing the initial steps of a method for operating a tandem mass spectrometer to perform glycoprotein identification using both CID and ExD, where CID and ExD analysis are performed in separate mass spectrometry experiments and the ExD analysis of precursor ions is based on finding glycan fragments in the CID analysis, in accordance with various embodiments. In step 210, one or more glycoproteins of a sample are digested.

In step 220, a precursor ion is fragmented using CID, and the CID product ions are analyzed producing a CID product ion spectrum. In the method of FIG. 10, the CID product ion spectrum is now used to determine the precursor ions for ExD analysis. As a result, this method includes step 1035. In step 1035, it is determined if a CID product ion spectrum includes glycan fragments. If it does, the precursor ion that produced the glycan fragment is added to the inclusion list of step 1036. Because the CID mass spectrometry experiment is used to build the precursor ion list for the ExD mass spectrometry experiment, it must occur before the ExD mass spectrometry experiment.

In step 230, after the experiment of step 220, only the precursor ions of the precursor ion inclusion list created in step 1036 are selected and then fragmented using ExD. The ExD product ions are analyzed producing an ExD product ion spectrum.

In comparison to the method of FIG. 2, the added steps 1035 and 1036 of the method of FIG. 10 reduce the number of ExD measurements needed for identifying glycopeptides. As a result, the method of FIG. 10 is more advantageous than the method of FIG. 2 for more complex samples that include compounds other than glycoproteins.

The remaining steps 221, 222, 223, 224, 225, 226, 227, and 231 perform the same functions as described with regard to FIG. 2. The other steps of FIG. 2, can also be performed using the method of FIG. 10.

Figure 11:
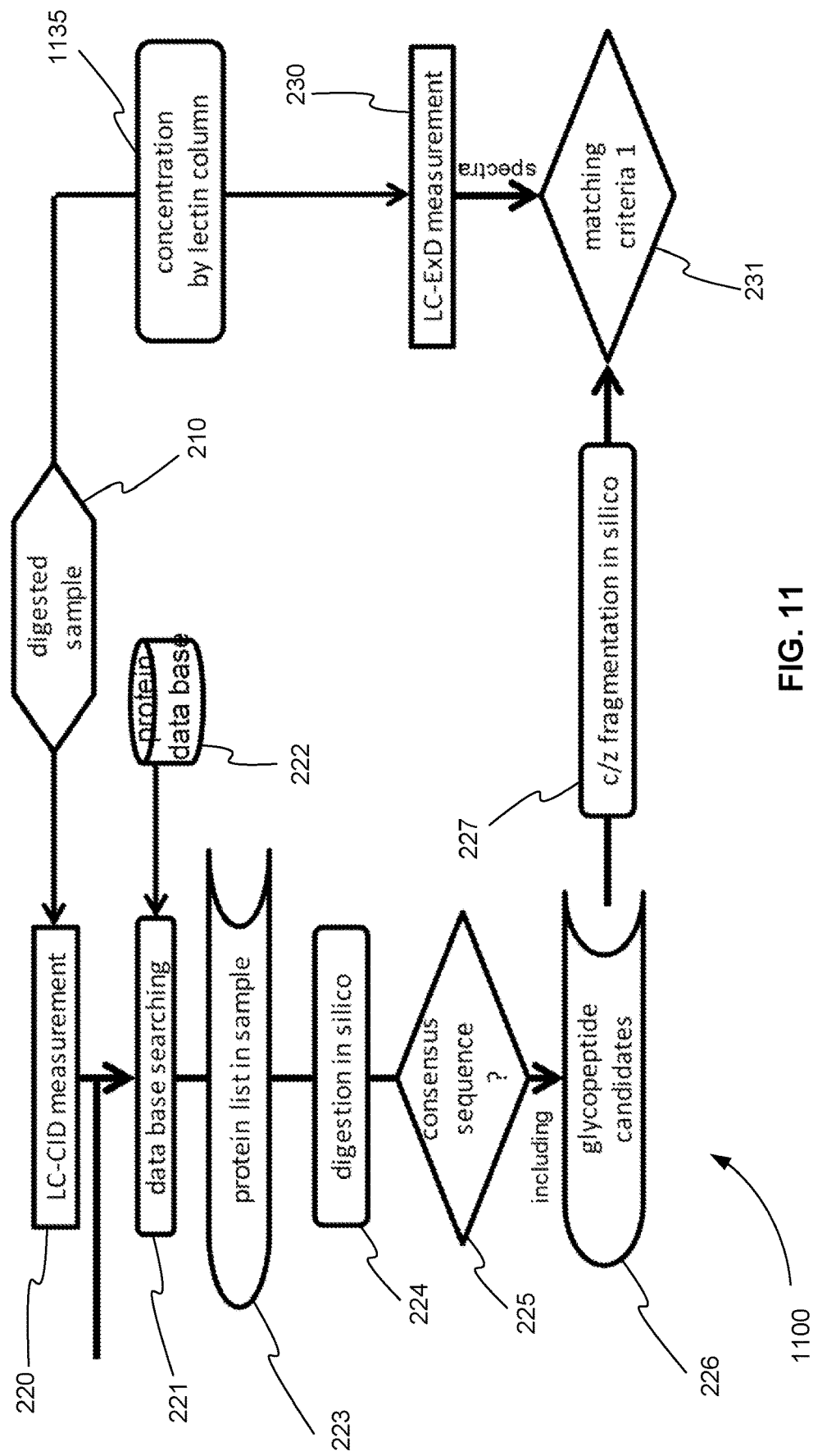
FIG. 11 is an exemplary flowchart showing the initial steps of a method for operating a tandem mass spectrometer to perform glycoprotein identification using both CID and ExD, where CID and ExD analysis are performed in separate mass spectrometry experiments and the ExD analysis further includes a glycosylation concentration method before ExD analysis, in accordance with various embodiments.

FIG. 11 is an exemplary flowchart 1100 showing the initial steps of a method for operating a tandem mass spectrometer to perform glycoprotein identification using both CID and ExD, where CID and ExD analysis are performed in separate mass spectrometry experiments and the ExD analysis further includes a glycosylation concentration method before ExD analysis, in accordance with various embodiments. Again, in step 210, one or more glycoproteins of a sample are digested.

In step 220, a precursor ion is fragmented using CID, and the CID product ions are analyzed producing a CID product ion spectrum. For a wide search of proteins, non-concentrated samples are for the CID measurement. As a result, the precursor ion fragmented using CID is obtained directly from the digested sample of step 210.

In contrast, for the ExD measurement, a glycosylation peptide concentration method is applied to the sample before ExD analysis. For example, the digested sample of step 210 is further subjected to glycosylation peptide concentration using the lectin column of step 1135 before LC injection. ExD may be less sensitive than CID, so concentrating the sample increases the sensitivity because it produces fewer ExD targets and more molecules of each target precursor ion. In step 230, a concentrated target precursor ion is fragmented using ExD, and the ExD product ions are analyzed producing an ExD product ion spectrum. The method of FIG. 11 provides a more glycopeptide specific ExD analysis, for example.

The remaining steps 221, 222, 223, 224, 225, 226, 227, and 231 perform the same functions as described with regard to FIG. 2. The other steps of FIG. 2, can also be performed using the method of FIG. 11.

Figure 12:
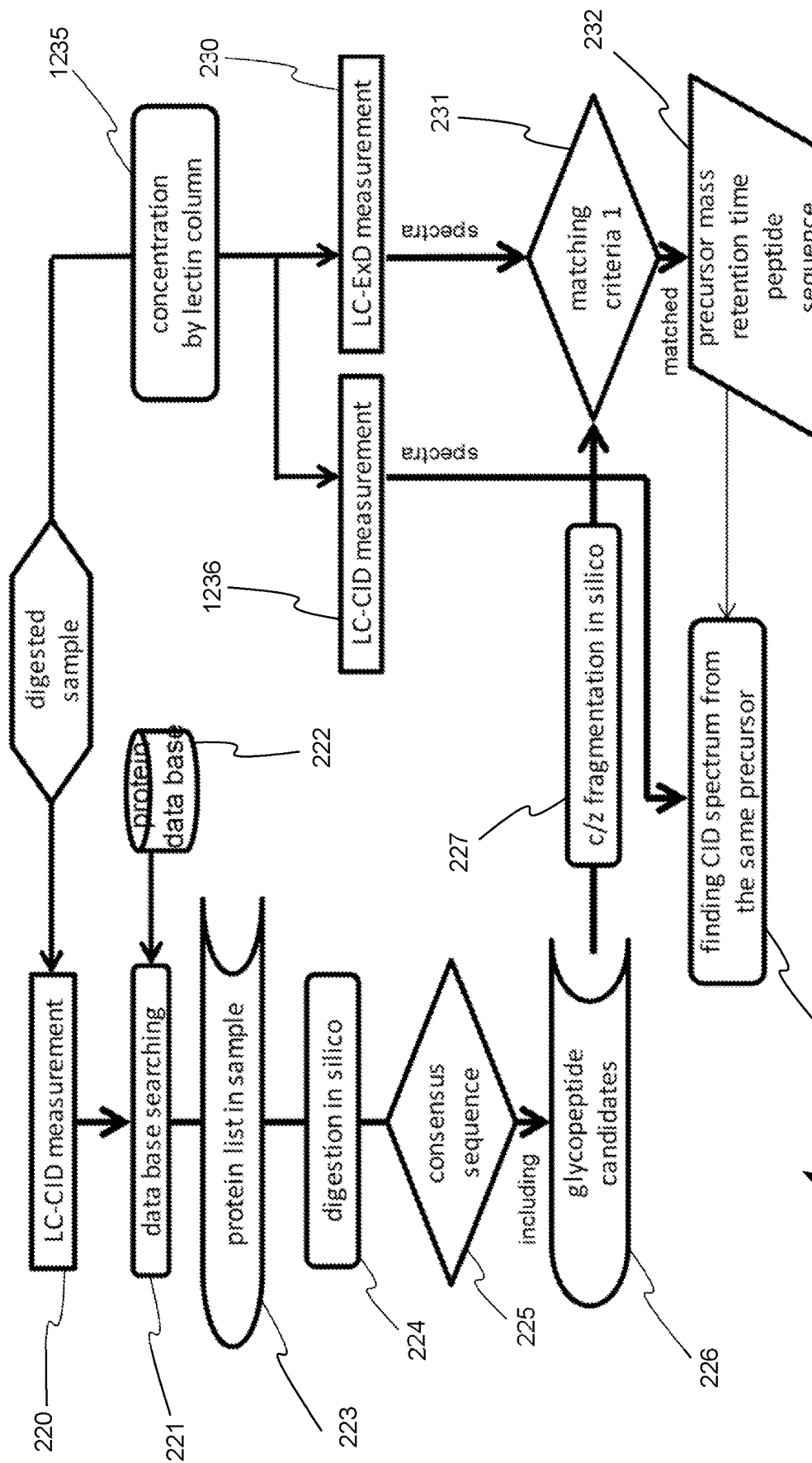
FIG. 12 is an exemplary flowchart showing the initial steps of a method for operating a tandem mass spectrometer to perform glycoprotein identification using both CID and ExD, where a first CID analysis, ExD analysis and a second CID analysis are performed in separate mass spectrometry experiments and the ExD analysis and the second CID analysis further include a glycosylation concentration method before the ExD analysis and the second CID analysis, in accordance with various embodiments.

FIG. 12 is an exemplary flowchart 1200 showing the initial steps of a method for operating a tandem mass spectrometer to perform glycoprotein identification using both CID and ExD, where a first CID analysis, ExD analysis and a second CID analysis are performed in separate mass spectrometry experiments and the ExD analysis and the second CID analysis further include a glycosylation concentration method before the ExD analysis and the second CID analysis, in accordance with various embodiments. Again, in step 210, one or more glycoproteins of a sample are digested.

In step 220, a precursor ion is fragmented in a first CID analysis, and the CID product ions are analyzed producing a first CID product ion spectrum. For a wide search of proteins, non-concentrated samples are for the CID measurement. As a result, the precursor ion fragmented using CID is obtained directly from the digested sample of step 210.

In contrast, for a second CID analysis and the ExD analysis, a glycosylation peptide concentration method is applied to the sample before the second CID analysis and the ExD analysis. For example, the digested sample of step 210 is further subjected to glycosylation peptide concentration using the lectin column of step 1235 before LC injection. ExD may be less sensitive than CID, so concentrating the sample increases the sensitivity because it produces fewer ExD targets and more molecules of each target precursor ion. In step 230, a concentrated target precursor ion is fragmented using ExD, and the ExD product ions are analyzed producing an ExD product ion spectrum.

A second CID analysis in step 1236 is also applied to the concentrated sample.

Second CID analysis in step 1236 provides a better signal-to-noise (S/N) measurement for the glycan fragments in the second CID product ion spectrum and this measurement is now used in step 244 instead of the measurement from step 220. As a result, reconstruction of a glycan structure from these glycan fragments is performed with a higher confidence. The method of FIG. 12 provides a more glycopeptide specific CID and ExD analysis, for example.

The remaining steps 221, 222, 223, 224, 225, 226, 227, 231, and 232 perform the same functions as described with regard to FIG. 2. The other steps of FIG. 2, can also be performed using the method of FIG. 12.

Figure 13:
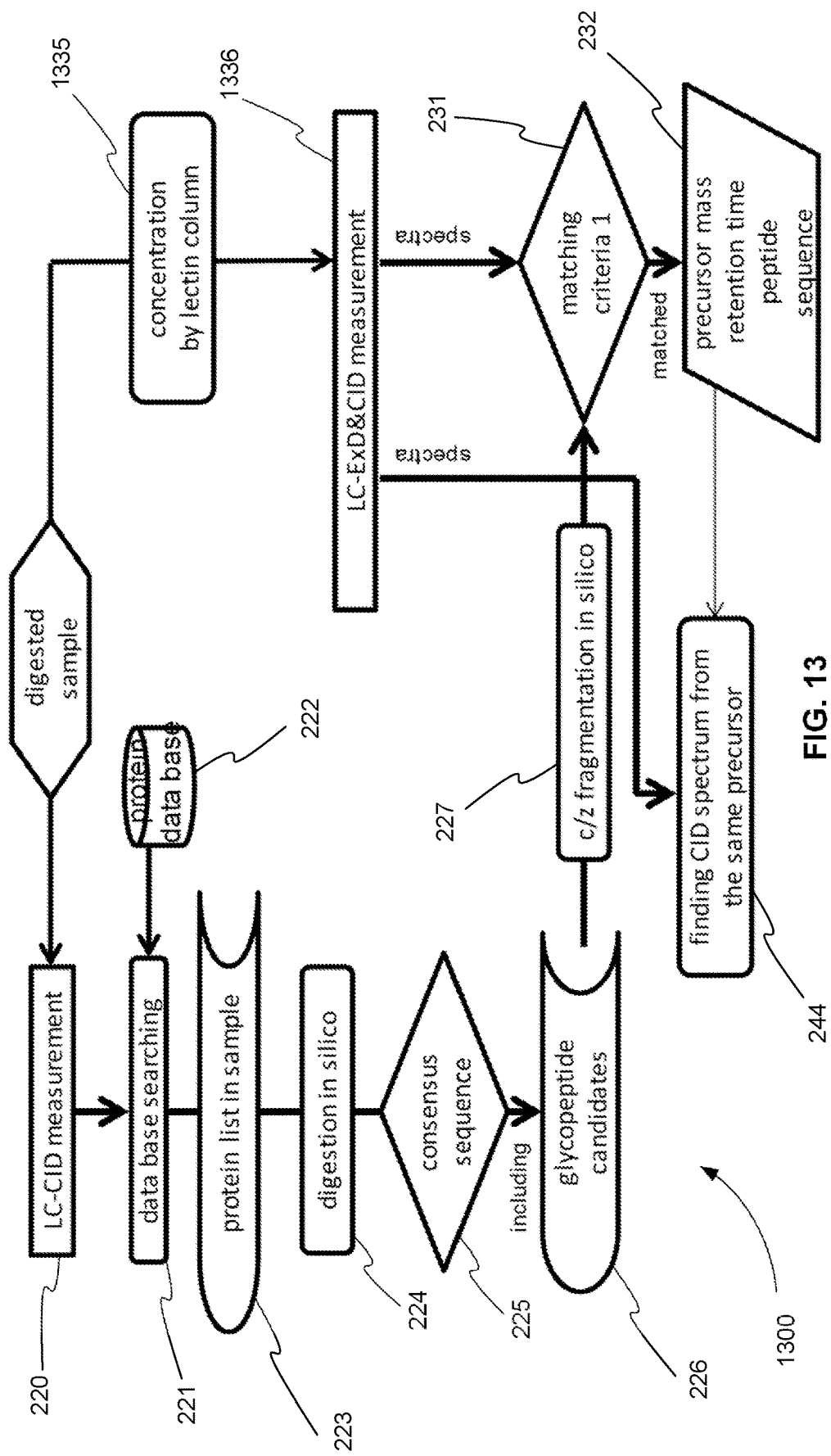
FIG. 13 is an exemplary flowchart showing the initial steps of a method for operating a tandem mass spectrometer to perform glycoprotein identification using both CID and ExD, where a first CID analysis is performed in a first mass spectrometry experiment and an ExD analysis and a second CID analysis are performed together in a second mass spectrometry experiment and the ExD analysis and the second CID analysis further include a glycosylation concentration method before the ExD analysis and the second CID analysis, in accordance with various embodiments.

FIG. 13 is an exemplary flowchart 1300 showing the initial steps of a method for operating a tandem mass spectrometer to perform glycoprotein identification using both CID and ExD, where a first CID analysis is performed in a first mass spectrometry experiment and an ExD analysis and a second CID analysis are performed together in a second mass spectrometry experiment and the ExD analysis and the second CID analysis further include a glycosylation concentration method before the ExD analysis and the second CID analysis, in accordance with various embodiments. Again, in step 210, one or more glycoproteins of a sample are digested.

In step 220, a precursor ion is fragmented in a first CID analysis, and the CID product ions are analyzed producing a first CID product ion spectrum. For a wide search of proteins, non-concentrated samples are for the CID measurement. As a result, the precursor ion fragmented using CID is obtained directly from the digested sample of step 210.

In contrast, for a second CID analysis and the ExD analysis, a glycosylation peptide concentration method is applied to the sample before the second CID analysis and the ExD analysis. For example, the digested sample of step 210 is further subjected to glycosylation peptide concentration using the lectin column of step 1235 before LC injection. ExD may be less sensitive than CID, so concentrating the sample increases the sensitivity because it produces fewer ExD targets and more molecules of each target precursor ion. The second CID analysis provides a better signal-to-noise (S/N) measurement for the glycan fragments in the second CID product ion spectrum, and this measurement is now used in step 244 instead of the measurement from step 220. As a result, reconstruction of a glycan structure from these glycan fragments is performed with a higher confidence.

In step 1336, the second CID analysis and the ExD analysis are now performed in the same LC-MSMS experiment. A concentrated target precursor ion is selected and then fragmented using CID, and the CID product ions are analyzed producing a second CID product ion spectrum. The same concentrated target precursor ion is selected and then fragmented using ExD, and the ExD product ions are analyzed producing an ExD product ion spectrum. The method of FIG. 13 is a preferred embodiment. However, like the method of FIG. 9, the method of FIG. 13 is performed with a modified IDA tandem mass spectrometry workflow.

The remaining steps 221, 222, 223, 224, 225, 226, 227, 231, and 232 perform the same functions as described with regard to FIG. 2. The other steps of FIG. 2, can also be performed using the method of FIG. 13.

System for Identifying a Peptide Sequence of a Glycopeptide

Figure 14:
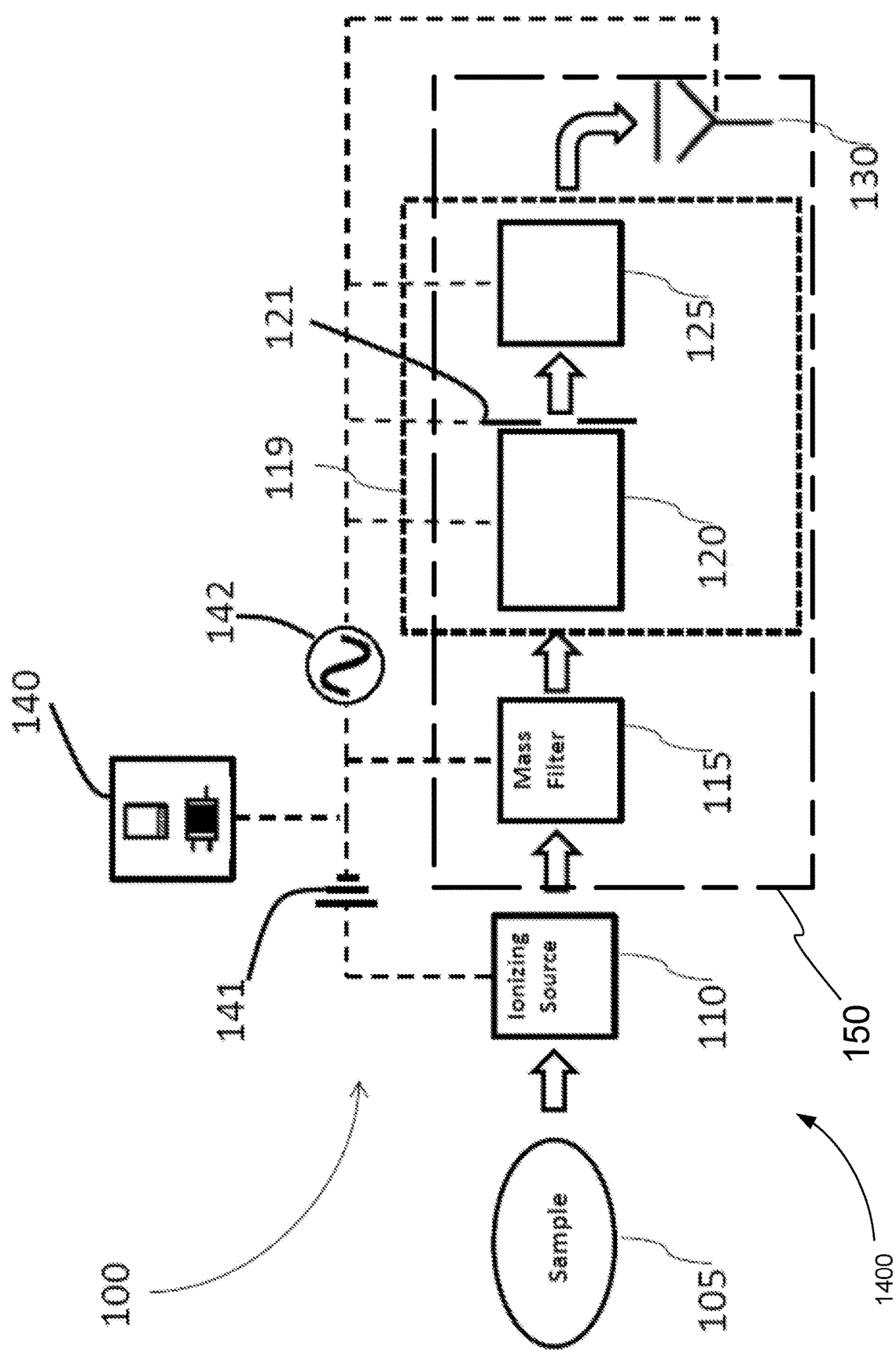
FIG. 14 is an exemplary schematic diagram of a system for operating tandem mass spectrometer to identify a peptide sequence of a glycopeptide of a sample, in accordance with various embodiments.

FIG. 14 is an exemplary schematic diagram 1400 of a system for operating tandem mass spectrometer to identify a peptide sequence of a glycopeptide of a sample, in accordance with various embodiments. The system of FIG. 14 includes an ion source device 110, a mass isolation device or filter 115, a first fragmentation device 120, second fragmentation device 125, a mass analyzer 130, and a processor 140.

Ion source device 110 can be any ion source device that is known in the art. In various embodiments, suitable ions sources can include, but should not be limited to, an electrospray ion source (ESI), an electron impact source and a fast atom bombardment source, an atmospheric pressure chemical ionization source (APCI), atmospheric pressure photoionization (APPI) source or a matrix assisted laser desorption source (MALDI). The ionization source can be chosen so as to preferably ionize glycopeptides. In a preferred embodiment, electrospray ionization is utilized.

Mass isolation device 115 is traditionally a quadrupole filter that has RF and DC voltages applied to it and whose capability to filter ions is modeled by the Mathieu equation. While in preferred embodiments, the mass isolation device 115 comprises a set of quadrupole rods, it should be appreciated that the term mass isolation device is intended to cover any mass spectrometer type device that is capable of filtering ions to produce an effect of isolating ions. For example, the mass isolation device may comprise an ion trap device that traps ions and functions to scan out ions having certain m/z values First fragmentation device 120 is capable of operating as either an ExD device or an ion guide. When operating as an ion guide, ions that enter the ExD device 125 from the multipole ion guide 120 are passed through to the exit of the ExD device 125 without reactions. When operating the device as an ExD device 125, the electrons being utilized may range in energy from approximately 1 eV to 15 eV, depending on the type of electron associated dissociation reaction that is desired. Electron based reactions that take place in the ExD device 125 can function to generate peptide fragments and perform cross-ring cleaving of glycans.

Second fragmentation device 125 may take the form of any multipole guide that operates like the Q2 region of a tandem mass spectrometer and operates as a collision cell. The collision cell is filled with a gas and is maintained at a high enough pressure and voltage so that multiple low energy collisions occur, which induces Collision Induced Dissociation (CID) of ions breaking parent ions into fragments. Depending on the energies provided to the collision cell and gases utilized, in certain embodiments of the invention, the multipole ion guide 120 operates to separate glycans from peptides, break peptides into fragments and/or break glycans into its component sugars.

In various embodiments, a lens electrode 121 may be placed between second fragmentation device 125 and first fragmentation device 120. Lens 121 is configured, for example, to extract ions trapped by first fragmentation device 122 and pass filtering. Also, in various embodiments, second fragmentation device 125, lens 121, and first fragmentation device 120 may be thought of as a single fragmentation device 119.

Mass analyzer 130 can be any types of mass spectrometers. In an embodiment, a final mass isolation device (Q3) consisting of a quadrupole filter and detector in a tandem mass spectrometer. In other embodiments, this last spectrometer may be a time-of-flight (TOF) mass spectrometer or an ion trap. In preferred embodiments, this last stage is a TOF device.

In various embodiments, mass isolation device 115, second fragmentation device 125, first fragmentation device 120, and mass analyzer 130 are components of a tandem mass spectrometer 150. In various alternative embodiments, ion source device 110 may also be considered a component of tandem mass spectrometer 150.

Processor 140 can be, but is not limited to, a controller, a computer, a microprocessor, the computer system of FIG. 1, or any device capable of sending and receiving control signals and data to and the components of tandem mass spectrometer 150 and processing data. Processor 140 is in communication with, at least, mass isolation device 115, second fragmentation device 125, first fragmentation device 120, and mass analyzer 130.

In various embodiments, the system of FIG. 14 further includes one or more power supplies, including, for example, DC power supply 141 and RF power supply 142. The one or more power supplies can be controlled by processor 140 so as to apply electric potentials with RF, AC, and/or DC components to electrodes of the various components to configure the elements of tandem mass spectrometer 150 in a coordinated fashion and/or for various different modes of operation.

Ion source device 110 adapted to receive and ionize a sample 105 that has been digested using a protease, producing an ion beam. Mass isolation device 115 of tandem mass spectrometer 150 or MS/MS 150 is adapted to select precursor ions from the ion beam of ion source device 110. Second fragmentation device 125 of MS/MS 150 is adapted to fragment selected precursor ions using collision-induced dissociation (CID) and to produce product ions. First fragmentation device 120 of MS/MS 150 is adapted to fragment selected precursor ions using electron-based dissociation (ExD) and to produce product ions. Mass analyzer 130 of MS/MS 150 is adapted to mass analyze product ions from second fragmentation device 125 or first fragmentation device 120 and produce a product ion spectrum.

Processor 140 performs a series of steps. In step (i), processor 140 instructs mass isolation device 115 to select at least one precursor ion from a first ion beam. In step (ii), processor 140 instructs second fragmentation device 125 to fragment the at least one precursor ion, producing a plurality of CID product ions. In step (iii), processor 140 instructs mass analyzer 130 to mass analyze the plurality of CID product ions, producing a first CID spectrum. In step (iv), processor 140 determines a list of one or more theoretical candidate glycopeptide sequences from the first CID spectrum.

In step (v), processor 140 instructs mass isolation device 115 to select again the at least one precursor ion from a second ion beam produced by the ion source device from the sample. In step (vi), processor 140 instructs first fragmentation device 120 to fragment the at least one precursor ion, producing a plurality of ExD product ions. In step (vii), processor 140 instructs mass analyzer 130 to mass analyze the plurality of ExD product ions, producing an ExD spectrum.

In step (viii), for each candidate sequence of the list of one or more theoretical candidate glycopeptide sequences, processor 140 computationally fragments the sequence using c and z fragment rules, producing a plurality of theoretical fragments, calculates mass-to-charge ratio (m/z) values for the plurality of theoretical fragments, and scores the sequence by (a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site, (b) not incrementing the score, for each m/z value of a product ion peak of the ExD spectrum that matches to an m/z value of a z fragment of the plurality of theoretical fragments from the N terminal side of the sequence to a consensus sequence of a glycan modification site, (c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and (d) incrementing the score, for each m/z value of a product ion peak of the ExD spectrum that matches to an m/z value of a z fragment of the plurality of theoretical fragments from the C terminal side of the sequence to a consensus sequence of a glycan modification site.

Finally, in step (ix), processor 140 identifies a candidate sequence of the list of one or more theoretical candidate glycopeptide sequences with the highest score as a peptide sequence of a glycopeptide of the sample.

In various embodiments, a consensus sequence of a glycan modification site includes O glycan consensus sequence S or T or N glycan consensus sequence NxT or NxS, where x≠P and S=Serine, T=Threonine, N=Asparagine, and P=Proline.

In various embodiments and as shown in FIG. 3, processor 140 determines a list of one or more theoretical candidate glycopeptide sequences from the first CID spectrum by matching the CID spectrum to a protein database. More specifically, processor 140 searches a protein database using the first CID spectrum, producing a list of proteins. Processor 140 computationally digests each protein of the protein list using cleavage rules of the protease used in the actual digestion, producing a list of theoretical peptide sequences. Processor 140 selects each theoretical glycopeptide sequence from the peptide sequence list that includes a consensus sequence of a glycan modification site, producing the list of one or more theoretical candidate glycopeptide sequences.

In various embodiments and in reference to FIG. 5, a separation device, such as a liquid chromatography (LC) device, is used in conjunction with the glycopeptide sequence identification. More specifically, the system of FIG. 14 further includes a separation device (not shown) that is adapted to separate peptides of the digested sample over time and introduce the separated peptides to ion source device 110. Processor 140 instructs mass isolation device 115 to select a mass range of precursor ions at a plurality of time steps. Processor 140 instructs mass analyzer 130 to mass analyze the mass range of precursor ions at the plurality of time steps, producing a chromatogram of precursor ion m/z, charge, and intensity values over time for each precursor ion the mass range of precursor ions. Processor 140 selects the at least one precursor ion from the chromatogram, wherein the m/z, charge, and intensity values of the at least one precursor ion are known from the chromatogram.

In various embodiments and in reference to step 241 of FIG. 7, processor 140 further calculates a post-translational modification (PTM) mass for the identified glycopeptide sequence. Processor 140 subtracts the theoretically calculated mass of the identified candidate sequence from the experimental mass of the at least one precursor ion found from the m/z and charge of the at least one precursor ion.

In various embodiments and in reference to step 242 of FIG. 7, processor 140 further validates the identified candidate sequence. Processor 140 adds the PTM mass to each of one or more consensus sequence glycan modification sites of the identified candidate sequence, producing one or more modified candidate sequences. Processor 140 theoretically fragments each of the one or more modified candidate sequences. Processor 140 scores each of the one or more modified candidate sequences by
 (a) incrementing a score of the sequence, for each m/z value of a product ion peak of the ExD spectrum that matches to an m/z value of a c fragment from the entire sequence and
 (b) incrementing a score of the sequence, for each m/z value of a product ion peak of the ExD spectrum that matches to an m/z value of a z fragment from the entire sequence.

Processor 140 validates the identified candidate sequence if a score of a modified candidate sequence exceeds the score of the identified candidate sequence. Further, if a score of a modified candidate sequence exceeds the score of the identified candidate sequence, processor 140 identifies the modification site of the modified candidate sequence as the modification site of the identified candidate sequence.

In various embodiments and in reference to step 245 of FIG. 7, processor 140 further determines a glycan structure of the glycopeptide of the sample by searching a database of glycan structures and their masses using the PTM mass. In another embodiment, processor 140 determines a glycan structure of the glycopeptide of the sample by searching a database of glycan structures and their masses and comparing the PTM mass to each mass of each glycan structure and comparing glycan fragments of the first CID spectrum to subunits of each glycan structure. In another embodiment, processor 140 determines a glycan structure of the glycopeptide of the sample by comparing the PTM mass to a mass of any combination of a list of component sugars. The list of component sugars can include Gal, Man, GlcNAC, GalNAc, Fuc, Neu5Gc, and Neu5Ac, for example.

In various embodiments and in reference to steps 220 and 230 of FIG. 2, processor 140 performs steps (i)-(iv) in a first tandem mass spectrometry experiment applied the to the sample and steps (v)-(ix) in a second tandem mass spectrometry experiment applied to the same sample.

In various embodiments and in reference to steps 1035 and 1036 of FIG. 10, processor 140 identifies one or more glycan fragments from the first CID spectrum and adds the at least one precursor ion to a precursor ion inclusion list for ExD analysis because it includes a glycan fragment. Processor 140 instructs mass isolation device 115 to select only select precursor ions in the second tandem mass spectrometry experiment from the inclusion list.

In various embodiments and in reference to step 1135 of FIG. 11, a glycosylation peptide concentration method is further applied to the digested sample before the second tandem mass spectrometry experiment, producing a concentrated digested sample. The second tandem mass spectrometry experiment is performed using the concentrated digested sample. The glycosylation peptide concentration is applied using a lectin column, for example.

In various embodiments and in reference to steps 1236 and 244 of FIG. 12, processor 140 further performs the following steps. In step (x), processor 140 instructs mass isolation device 115 to select the same at least one precursor ion from a third ion beam. In step (xi), processor 140 instructs second fragmentation device 125 to fragment the at least one precursor ion, producing a second plurality of CID product ions. In step (xii), processor 140 instructs mass analyzer 130 to mass analyze the second plurality of CID product ions, producing a second CID spectrum. In step (xiii), processor 140 determines a glycan structure of the glycopeptide of the sample by searching a database of glycan structures and their masses and comparing glycan fragments of the second CID spectrum to subunits of each glycan structure. Processor 140 performs steps (x)-(xiii) in a third tandem mass spectrometry experiment applied to the concentrated digested sample.

In various embodiments and in reference to step 1336 of FIG. 13, the second ion beam and the third ion beam are the same ion beam and processor 140 performs steps (v)-(ix) and steps (x)-(xiii) in the second tandem mass spectrometry experiment applied to the concentrated digested sample.

In various embodiments and in reference to step 920 of FIG. 9, the first ion beam and the second ion beam are the same ion beam and processor 140 performs steps (i)-(iv) and steps (v)-(ix) in the same tandem mass spectrometry experiment applied to the sample.

Method for Identifying a Peptide Sequence of a Glycopeptide

Figure 15:
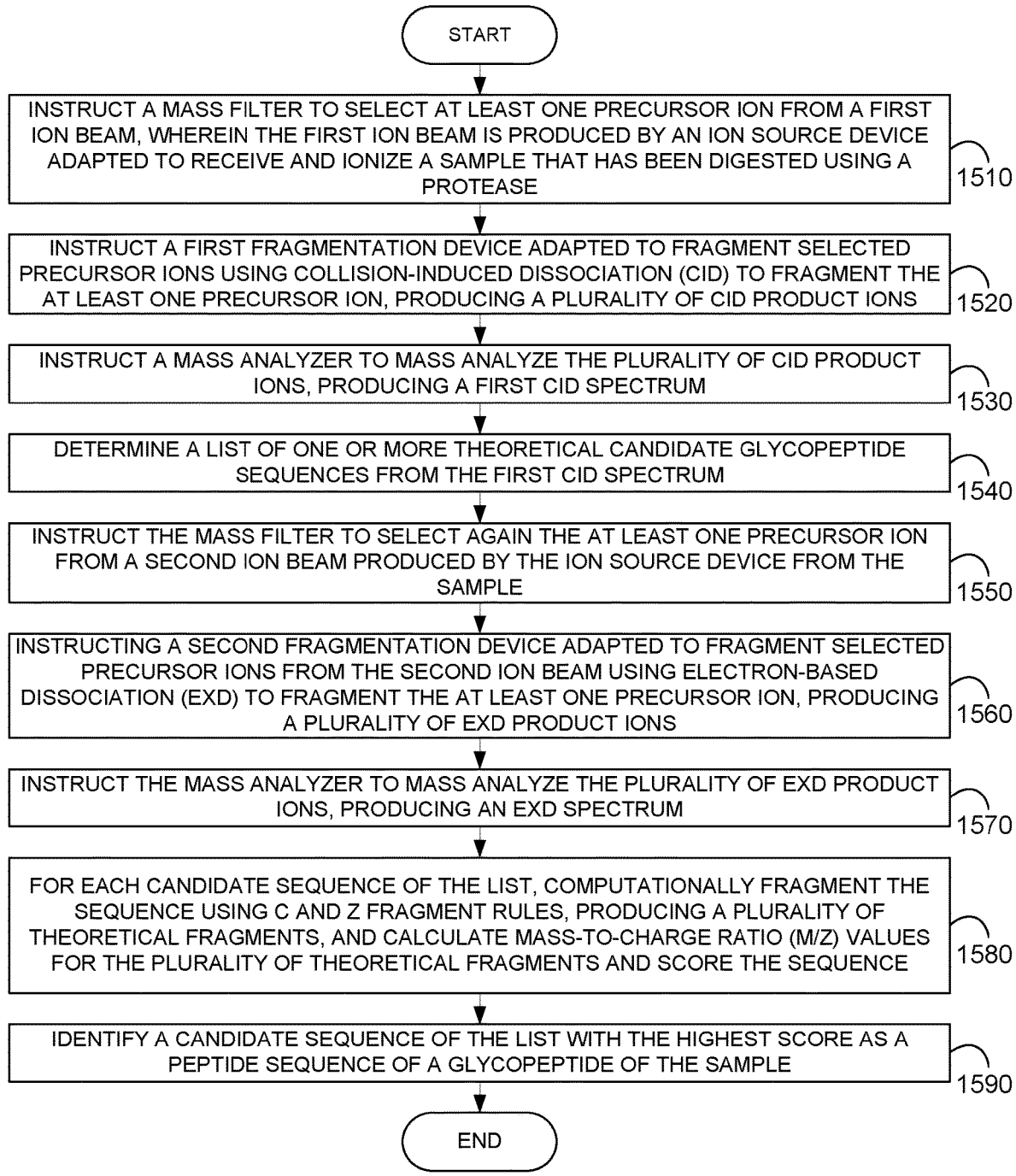
FIG. 15 is a method for operating tandem mass spectrometer to identify a peptide sequence of a glycopeptide of a sample, in accordance with various embodiments.

FIG. 15 is a method 1500 for operating tandem mass spectrometer to identify an peptide sequence of a glycopeptide of a sample, in accordance with various embodiments.

In step 1510 of method 1500, a mass isolation device of a tandem mass spectrometer (MS/MS) is instructed to select at least one precursor ion from a first ion beam using a processor. The first ion beam is produced by an ion source device adapted to receive and ionize a sample that has been digested using a protease.

In step 1520, a first fragmentation device of the MS/MS that is adapted to fragment selected precursor ions using collision-induced dissociation (CID) is instructed to fragment the at least one precursor ion using the processor, producing a plurality of CID product ions.

In step 1530, a mass analyzer of the MS/MS is instructed to mass analyze the plurality of CID product ions using the processor, producing a first CID spectrum.

In step 1540, a list of one or more theoretical candidate glycopeptide sequences is determined from the first CID spectrum using the processor.

In step 1550, the mass isolation device is instructed to select again the at least one precursor ion from a second ion beam produced by the ion source device from the sample using the processor.

In step 1560, a second fragmentation device of the MS/MS that is adapted to fragment selected precursor ions from the second ion beam using electron-based dissociation (ExD) is instructed to fragment the at least one precursor ion using the processor, producing a plurality of ExD product ions.

In step 1570, the mass analyzer is instructed to mass analyze the plurality of ExD product ions using the processor, producing an ExD spectrum.

In step 1580, for each candidate sequence of the list, the sequence is computationally fragmented using c and z fragment rules, producing a plurality of theoretical fragments, mass-to-charge ratio (m/z) values are calculated for the plurality of theoretical fragments, and the sequence is scored using the processor. The sequence is scored by (c) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site, (d) not incrementing the score, for each m/z value of a product ion peak of the ExD spectrum that matches to an m/z value of a z fragment of the plurality of theoretical fragments from the N terminal side of the sequence to a consensus sequence of a glycan modification site, (c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and (d) incrementing the score, for each m/z value of a product ion peak of the ExD spectrum that matches to an m/z value of a z fragment of the plurality of theoretical fragments from the C terminal side of the sequence to a consensus sequence of a glycan modification site.

In step 1580, a candidate sequence of the list with the highest score is identified as a peptide sequence of a glycopeptide of the sample using the processor.

Computer Program Product for Identifying a Peptide Sequence of a Glycopeptide

In various embodiments, a computer program product includes a non-transitory tangible computer-readable storage medium whose contents include a program with instructions being executed on a processor so as to perform a method for operating tandem mass spectrometer to identify a peptide sequence of a glycopeptide of a sample. This method is performed by a system that includes one or more distinct software modules.

Figure 16:
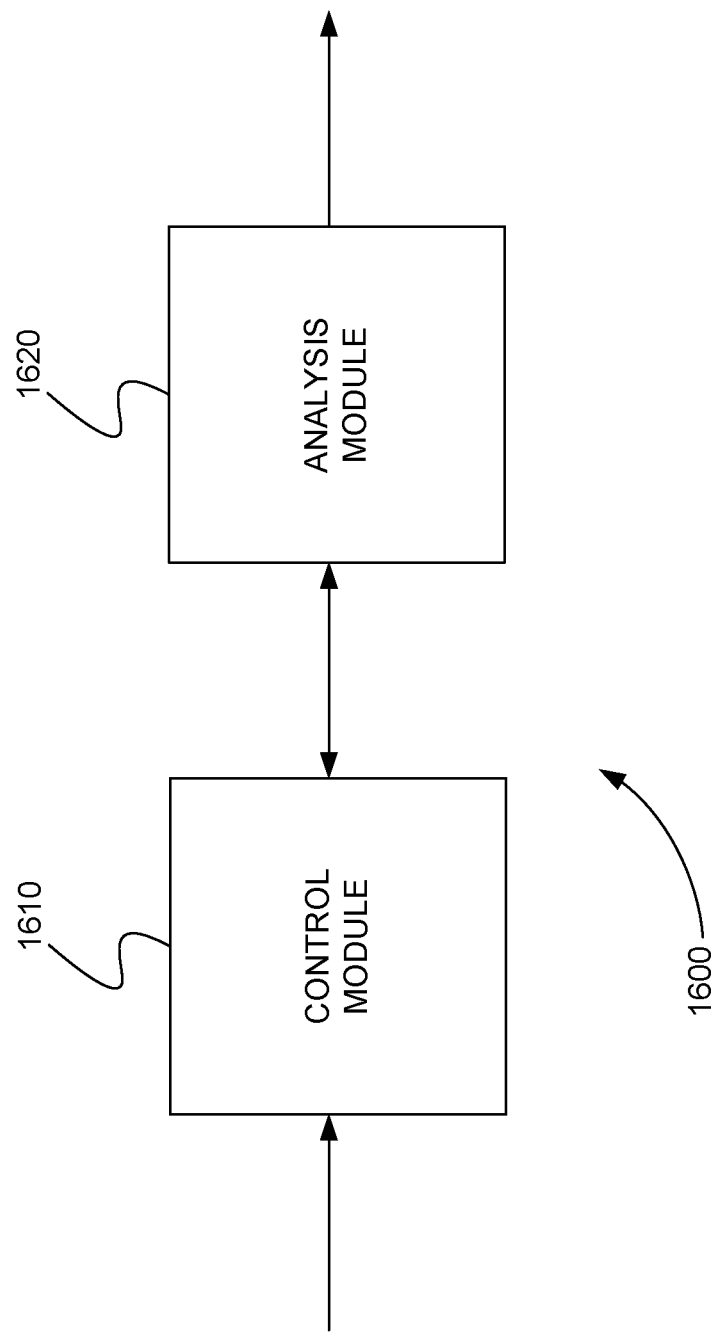
FIG. 16 is a schematic diagram of a system that includes one or more distinct software modules that performs a method for operating tandem mass spectrometer to identify a peptide sequence of a glycopeptide of a sample, in accordance with various embodiments.

FIG. 16 is a schematic diagram of a system 1600 that includes one or more distinct software modules that performs a method for operating tandem mass spectrometer to identify a peptide sequence of a glycopeptide of a sample, in accordance with various embodiments. System 1600 includes control module 1610 and analysis module 1620.

Control module 1610 instructs a mass isolation device of a tandem mass spectrometer (MS/MS) to select at least one precursor ion from a first ion beam. The ion beam is produced by an ion source device adapted to receive and ionize a sample that has been digested using a protease. Control module 1610 instructs a first fragmentation device of the MS/MS that is adapted to fragment selected precursor ions using collision-induced dissociation (CID) to fragment the at least one precursor ion, producing a plurality of CID product ions. Control module 1610 instructs a mass analyzer of the MS/MS to mass analyze the plurality of CID product ions, producing a first CID spectrum.

Analysis module 1620 determines a list of one or more theoretical candidate glycopeptide sequences from the first CID spectrum.

Control module 1610 instructs the mass isolation device to select again the at least one precursor ion from a second ion beam produced by the ion source device from the sample. Control module 1610 instructs a second fragmentation device of the MS/MS that is adapted to fragment selected precursor ions from the second ion beam using electron-based dissociation (ExD) to fragment the at least one precursor ion, producing a plurality of ExD product ions. Control module 1610 instructs the mass analyzer to mass analyze the plurality of ExD product ions, producing an ExD spectrum.

For each candidate sequence of the list, analysis module 1620 computationally fragments the sequence using c and z fragment rules, producing a plurality of theoretical fragments, and calculates mass-to-charge ratio (m/z) values for the plurality of theoretical fragments and analysis module 1620 scores the sequence. Analysis module 1620 scores the sequence by (a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site, (b) not incrementing the score, for each m/z value of a product ion peak of the ExD spectrum that matches to an m/z value of a z fragment of the plurality of theoretical fragments from the N terminal side of the sequence to a consensus sequence of a glycan modification site, (c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and (d) incrementing the score, for each m/z value of a product ion peak of the ExD spectrum that matches to an m/z value of a z fragment of the plurality of theoretical fragments from the C terminal side of the sequence to a consensus sequence of a glycan modification site.

Analysis module 1620 identifies a candidate sequence of the list with the highest score as a peptide sequence of a glycopeptide of the sample.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for operating tandem mass spectrometer to identify a peptide sequence of a glycopeptide, comprising:
an ion source device adapted to receive and ionize a sample that has been digested using a protease, producing an ion beam;
a mass isolation device of a tandem mass spectrometer (MS/MS) adapted to select precursor ions from the ion beam of the ion source device;
a first fragmentation device of the MS/MS adapted to fragment selected precursor ions using collision-induced dissociation (CID) and to produce product ions;
a second fragmentation device of the MS/MS adapted to fragment selected precursor ions using electron-based dissociation (ExD) and to produce product ions;
a mass analyzer of the MS/MS adapted to mass analyze product ions from the first or second fragmentation device and produce a product ion spectrum; and
a processor in communication with that tandem mass spectrometer that
(i) instructs the mass isolation device to select at least one precursor ion from a first ion beam,
(ii) instructs the first fragmentation device to fragment the at least one precursor ion, producing a plurality of CID product ions,
(iii) instructs the mass analyzer to mass analyze the plurality of CID product ions, producing a first CID spectrum,
(iv) determines a list of one or more theoretical candidate glycopeptide sequences from the first CID spectrum,
(v) instructs the mass isolation device to select again the at least one precursor ion from a second ion beam produced by the ion source device from the sample,
(vi) instructs the second fragmentation device to fragment the at least one precursor ion, producing a plurality of ExD product ions,
(vii) instructs the mass analyzer to mass analyze the plurality of ExD product ions, producing an ExD spectrum,
(viii) for each candidate sequence of the list, computationally fragments the sequence using c and z fragment rules, producing a plurality of theoretical fragments, calculates mass-to-charge ratio (m/z) values for the plurality of theoretical fragments, and scores the sequence by
(a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site,
(b) not incrementing the score, for each m/z value of a product ion peak of the ExD spectrum that matches to an m/z value of a z fragment of the plurality of theoretical fragments from the N terminal side of the sequence to a consensus sequence of a glycan modification site,
(c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and
(d) incrementing the score, for each m/z value of a product ion peak of the ExD spectrum that matches to an m/z value of a z fragment of the plurality of theoretical fragments from the C terminal side of the sequence to a consensus sequence of a glycan modification site, and
(ix) identifies a candidate sequence of the list with the highest score as the peptide sequence of the glycopeptide.

2. The system of claim 1, wherein the consensus sequence of a glycan modification site includes O glycan consensus sequence S or T or N glycan consensus sequence NxT or NxS, where $x \neq P$ and S=Serine, T=Threonine, N=Asparagine, and P=Proline.

3. The system of claim 1, wherein the processor determines the list of one or more theoretical candidate glycopeptide sequences by
searching a protein database using the first CID spectrum, producing a list of proteins, computationally digesting each protein of the protein list using cleavage rules of the protease, producing a list of theoretical peptide sequences,
selecting each theoretical glycopeptide sequence from the peptide sequence list that includes the consensus sequence of a glycan modification site, producing the list of one or more theoretical candidate glycopeptide sequences.

4. The system of claim 1, further comprising
a separation device adapted to separate peptides of the sample over time and introduce the separated peptides to the ion source device, wherein the processor further instructs the mass isolation device to select a mass range of precursor ions at a plurality of time steps, instructs the mass analyzer to mass analyze the mass range of precursor ions at the plurality of time steps, producing a chromatogram of precursor ion m/z, charge, and intensity values over time for each precursor ion the mass range of precursor ions, and selects the at least one precursor ion from the chromatogram, wherein the m/z, charge, and intensity values of the at least one precursor ion are known from the chromatogram.

5. The system of claim 4, wherein the processor further calculates a post translational modification (PTM) mass by subtracting the theoretically calculated mass of the identified candidate sequence from the experimental mass of the at least one precursor ion found from the m/z and charge of the at least one precursor ion.

6. The system of claim 5, wherein the processor further validates the identified candidate sequence with the highest score by
adding the PTM mass to each of one or more consensus sequence glycan modification sites of the identified candidate sequence, producing one or more modified candidate sequences, and theoretically fragmenting each of the one or more modified candidate sequences,
scoring each of the one or more modified candidate sequences by
(a) incrementing a score of the sequence, for each m/z value of a product ion peak of the ExD spectrum that matches to an m/z value of a c fragment from the entire sequence and
(b) incrementing a score of the sequence, for each m/z value of a product ion peak of the ExD spectrum that matches to an m/z value of a z fragment from the entire sequence, and validating the identified candidate sequence if a score of a modified candidate sequence exceeds the score of the identified candidate sequence.

7. The system of claim 6, wherein if a score of a modified candidate sequence exceeds the score of the identified candidate sequence, the processor identifies the modification site of the modified candidate sequence as the modification site of the identified candidate sequence.

8. The system of claim 5, wherein the processor further determines a glycan structure of the glycopeptide by searching a database of glycan structures and their masses using the PTM mass.

9. The system of claim 5, wherein the processor further determines a glycan structure of the glycopeptide by searching a database of glycan structures and their masses and comparing the PTM mass to each mass of each glycan structure and comparing glycan fragments of the first CID spectrum to subunits of each glycan structure.

10. The system of claim 5, wherein the processor further determines a glycan structure of the glycopeptide by comparing the PTM mass to a mass of any combination of a list of component sugars.

11. The system of claim 10, wherein the list of component sugars can include Gal, Man, GlcNAC, GalNAc, Fuc, Neu5Gc, and Neu5Ac.

12. The system of claim 1, wherein the processor performs steps (i)-(iv) in a first tandem mass spectrometry experiment applied to the sample and steps (v)-(ix) in a second tandem mass spectrometry experiment applied to the sample.

13. The system of claim 12, wherein the processor further identifies one or more glycan fragments from the first CID spectrum and adds the at least one precursor ion to a precursor ion inclusion list for ExD analysis because it includes a glycan fragment and instructs the mass isolation device to select only select precursor ions in the second tandem mass spectrometry experiment from the inclusion list.

14. The system of claim 12, wherein a glycosylation peptide concentration method is further applied to the sample before the second tandem mass spectrometry experiment, producing a concentrated sample, and the second tandem mass spectrometry experiment is performed using the concentrated sample.

15. The system of claim 14, wherein the glycosylation peptide concentration is applied using a lectin column.

16. The system of claim 14, wherein the processor further
(x) instructs the mass isolation device to select the same at least one precursor ion from a third ion beam,
(xi) instructs the first fragmentation device to fragment the at least one precursor ion, producing a second plurality of CID product ions,
(xii) instructs the mass analyzer to mass analyze the second plurality of CID product ions, producing a second CID spectrum, and
(xiii) determines a glycan structure of the glycopeptide by searching a database of glycan structures and their masses and comparing glycan fragments of the second CID spectrum to subunits of each glycan structure.

17. The system of claim 16, wherein the processor performs steps (x)-(xiii) in a third tandem mass spectrometry experiment applied to the concentrated sample.

18. The system of claim 16, wherein the second ion beam and the third ion beam are the same ion beam and the processor performs steps (v)-(ix) and steps (x)-(xiii) in the second tandem mass spectrometry experiment applied to the concentrated sample.

19. The system of claim 1, wherein the first ion beam and the second ion beam are the same ion beam and the processor performs steps (i)-(iv) and steps (v)-(ix) in the same tandem mass spectrometry experiment applied to the sample.

20. A method for operating tandem mass spectrometer to identify a peptide sequence of a glycopeptide, comprising:
instructing a mass isolation device of a tandem mass spectrometer (MS/MS) to select at least one precursor ion from a first ion beam using a processor, wherein the first ion beam is produced by an ion source device adapted to receive and ionize a sample that has been digested using a protease;
instructing a first fragmentation device of the MS/MS that is adapted to fragment selected precursor ions using collision-induced dissociation (CID) to fragment the at least one precursor ion using the processor, producing a plurality of CID product ions;
instructing a mass analyzer of the MS/MS to mass analyze the plurality of CID product ions using the processor, producing a first CID spectrum;
determining a list of one or more theoretical candidate glycopeptide sequences from the first CID spectrum using the processor;
instructing the mass isolation device to select again the at least one precursor ion from a second ion beam produced by the ion source device from the sample using the processor;
instructing a second fragmentation device of the MS/MS that is adapted to fragment selected precursor ions from the second ion beam using electron-based dissociation (ExD) to fragment the at least one precursor ion using the processor, producing a plurality of ExD product ions, instructing the mass analyzer to mass analyze the plurality of ExD product ions using the processor, producing an ExD spectrum;
for each candidate sequence of the list, computationally fragmenting the sequence using c and z fragment rules, producing a plurality of theoretical fragments, calculating mass-to-charge ratio (m/z) values for the plurality of theoretical fragments, and scoring the sequence using the processor by
(a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site,
(b) not incrementing the score, for each m/z value of a product ion peak of the ExD spectrum that matches to an m/z value of a z fragment of the plurality of theoretical fragments from the N terminal side of the sequence to a consensus sequence of a glycan modification site,
(c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and
(d) incrementing the score, for each m/z value of a product ion peak of the ExD spectrum that matches to an m/z value of a z fragment of the plurality of theoretical fragments from the C terminal side of the sequence to a consensus sequence of a glycan modification site; and identifying a candidate sequence of the list with the highest score as the peptide sequence of the glycopeptide using the processor.

21. A computer program product, comprising a non-transitory tangible computer-readable storage medium whose contents include a program with instructions being executed on a processor so as to perform a method for operating tandem mass spectrometer to identify a peptide sequence of a glycopeptide, comprising:

provec a system, wherein the system comprises one or more distinct software modules, and wherein the distinct software modules comprise a control module and an analysis module;

instructing a mass isolation device of a tandem mass spectrometer (MS/MS) to select at least one precursor ion from a first ion beam using the control module, wherein the ion beam is produced by an ion source device adapted to receive and ionize a sample that has been digested using a protease;

instructing a first fragmentation device of the MS/MS that is adapted to fragment selected precursor ions using collision-induced dissociation (CID) to fragment the at least one precursor ion using the control module, producing a plurality of CID product ions;

instructing a mass analyzer of the MS/MS to mass analyze the plurality of CID product ions using the control module, producing a first CID spectrum;

determining a list of one or more theoretical candidate glycopeptide sequences from the first CID spectrum using the analysis module;

instructing the mass isolation device to select again the at least one precursor ion from a second ion beam produced by the ion source device from the sample using the control module;

instructing a second fragmentation device of the MS/MS that is adapted to fragment selected precursor ions from the second ion beam using electron-based dissociation (ExD) to fragment the at least one precursor ion using the control module, producing a plurality of ExD product ions, instructing the mass analyzer to mass analyze the plurality of ExD product ions using the control module, producing an ExD spectrum;

for each candidate sequence of the list, computationally fragmenting the sequence using c and z fragment rules, producing a plurality of theoretical fragments, calculating mass-to-charge ratio (m/z) values for the plurality of theoretical fragments, and scoring the sequence using the analysis module by (a) incrementing a score of the sequence, for each m/z value of a product ion peak of the ExD spectrum that matches to an m/z value of a c fragment of the plurality of theoretical fragments from the N terminal side of the sequence to a consensus sequence of a glycan modification site, (b) not incrementing the score, for each m/z value of a product ion peak of the ExD spectrum that matches to an m/z value of a z fragment of the plurality of theoretical fragments from the N terminal side of the sequence to a consensus sequence of a glycan modification site, (c) not incrementing the score, for each m/z value of a product ion peak of the ExD spectrum that matches to an m/z value of a c fragment of the plurality of theoretical fragments from the C terminal side of the sequence to a consensus sequence of a glycan modification site, and (d) incrementing the score, for each m/z value of a product ion peak of the ExD spectrum that matches to an m/z value of a z fragment of the plurality of theoretical fragments from the C terminal side of the sequence to a consensus sequence of a glycan modification site; and identifying a candidate sequence of the list with the highest score as the peptide sequence of the glycopeptide using the analysis module.

* * * * *